(12) United States Patent
Ensor et al.

(10) Patent No.: US 11,714,075 B2
(45) Date of Patent: Aug. 1, 2023

(54) ENCASED POLYMER NANOFIBER-BASED ELECTRONIC NOSE

(71) Applicant: Research Triangle Institute, Research Triangle Park, NC (US)

(72) Inventors: David S. Ensor, Chapel Hill, NC (US); Li Han, Research Triangle Park, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 322 days.

(21) Appl. No.: 17/032,614

(22) Filed: Sep. 25, 2020

(65) Prior Publication Data

US 2021/0181172 A1   Jun. 17, 2021

Related U.S. Application Data

(63) Continuation of application No. 16/580,683, filed on Sep. 24, 2019, now Pat. No. 10,845,349, which is a continuation of application No. 14/654,292, filed as application No. PCT/US2013/076052 on Dec. 18, 2013, now abandoned.

(60) Provisional application No. 61/745,023, filed on Dec. 21, 2012.

(51) Int. Cl.
*G01N 33/00* (2006.01)
*G01N 27/12* (2006.01)
*G01N 27/22* (2006.01)

(52) U.S. Cl.
CPC ....... *G01N 33/0047* (2013.01); *G01N 27/127* (2013.01); *G01N 27/227* (2013.01)

(58) Field of Classification Search
CPC . G01N 33/0047; G01N 27/127; G01N 27/227
See application file for complete search history.

(56) References Cited

U.S. PATENT DOCUMENTS

| 5,571,401 A | 11/1996 | Lewis et al. |
| 5,698,089 A | 12/1997 | Lewis et al. |
| 5,788,833 A | 8/1998 | Lewis et al. |

(Continued)

OTHER PUBLICATIONS

Kedem, S., et al. "Enhanced stability effect in composite polymeric nanofibers containing titanium dioxide and carbon nanotubes." The Journal of Physical Chemistry C 113.33 (2009): 14893-14899. (Year: 2009).*

(Continued)

*Primary Examiner* — Robert J Eom
(74) *Attorney, Agent, or Firm* — IP & T Group LLP

(57) ABSTRACT

A chemical sensor and a system and method for sensing a chemical species. The chemical sensor includes a plurality of nanofibers whose electrical impedance varies upon exposure to the chemical species, a substrate supporting and electrically isolating the fibers, a set of electrodes connected to the plurality of fibers at spatially separated points to permit the electrical impedance of the plurality of fibers to be measured, and a membrane encasing the fibers and having a thickness ranging from 50 μm to 5.0 mm. The system includes the chemical sensor, an impedance measuring device coupled to the electrodes and configured to determine an electrical impedance of the plurality of fibers, and an analyzer configured to identify the chemical species based on a change in the electrical impedance.

20 Claims, 13 Drawing Sheets

(56) References Cited

U.S. PATENT DOCUMENTS

| | | | |
|---|---|---|---|
| 5,891,398 | A | 4/1999 | Lewis et al. |
| 5,911,872 | A | 6/1999 | Lewis et al. |
| 5,951,846 | A | 9/1999 | Lewis et al. |
| 5,959,191 | A | 9/1999 | Lewis et al. |
| 6,010,616 | A | 1/2000 | Lewis et al. |
| 6,013,229 | A | 1/2000 | Lewis et al. |
| 6,017,440 | A | 1/2000 | Lewis et al. |
| 6,093,308 | A | 7/2000 | Lewis et al. |
| 6,170,318 | B1 | 1/2001 | Lewis |
| 6,331,244 | B1 | 12/2001 | Lewis et al. |
| 6,537,498 | B1 | 3/2003 | Lewis et al. |
| 7,186,356 | B2 | 3/2007 | Lussey et al. |
| 7,955,561 | B2 | 6/2011 | Lewis et al. |
| 8,052,932 | B2 | 11/2011 | Han et al. |
| 8,460,790 | B2 | 6/2013 | Ochi et al. |
| 8,551,407 | B2 | 10/2013 | Friedrich et al. |
| 2001/0039824 | A1 | 11/2001 | Sunshine et al. |
| 2003/0159927 | A1 | 8/2003 | Lewis et al. |
| 2004/0033165 | A1 | 2/2004 | Lewis et al. |
| 2004/0217331 | A1 | 11/2004 | Lussey et al. |
| 2005/0241935 | A1 | 11/2005 | Lewis et al. |
| 2006/0034731 | A1 | 2/2006 | Lewis et al. |
| 2006/0057350 | A1 | 3/2006 | Ochi et al. |
| 2007/0114138 | A1 | 5/2007 | Krasteva et al. |
| 2008/0116908 | A1* | 5/2008 | Potyrailo ............. G21C 17/022 324/721 |
| 2008/0150556 | A1 | 6/2008 | Han et al. |
| 2008/0236251 | A1 | 10/2008 | Tepper et al. |
| 2009/0142852 | A1 | 6/2009 | Friedrich et al. |
| 2010/0039126 | A1 | 2/2010 | Chen et al. |
| 2011/0183563 | A1 | 7/2011 | Ochi et al. |
| 2012/0049864 | A1 | 3/2012 | Han et al. |

OTHER PUBLICATIONS

Weremczuk, Jerzy, Grzegorz Tarapata, and Ryszard Jachowicz. "Humidity sensor printed on textile with use of ink-jet technology." Procedia engineering 47 (2012): 1366-1369. (Year: 2012).*

Seesaard, Thara, Panida Lorwongtragool, and Teerakiat Kerdcharoen. "Wearable electronic nose based on embroidered amine sensors on the fabric substrates." 2012 9th International Conference on Electrical Engineering/Electronics, Computer, Telecommunications and Information Technology. IEEE, 2012. (Year: 2012).*

Cotton, Darryl P. J. et al. 2009. "A Multifunctional Capacitive Sensor for Stretchable Electronic Skins." IEEE Sensors Journal, vol. 9, No. 12, p. 2008-2009.

Elbuken, Caglar et al. 2011. "Detection of microdroplet size and speed using capacitive sensors." Sensors and Actuators A 171. p. 55-62.

Merkel, T. C. et al. 2000. "Gas Sorption, Diffusion, and Permeation in Poly(dimethylsiloxane)." Journal of Polymer Science: Part B: Polymer Physics. vol. 38, p. 415-434.

Non-Final Office Action issued by USPTO in reference to related U.S. Appl. No. 16/580,683, dated Apr. 7, 2020 (12 pages).

* cited by examiner

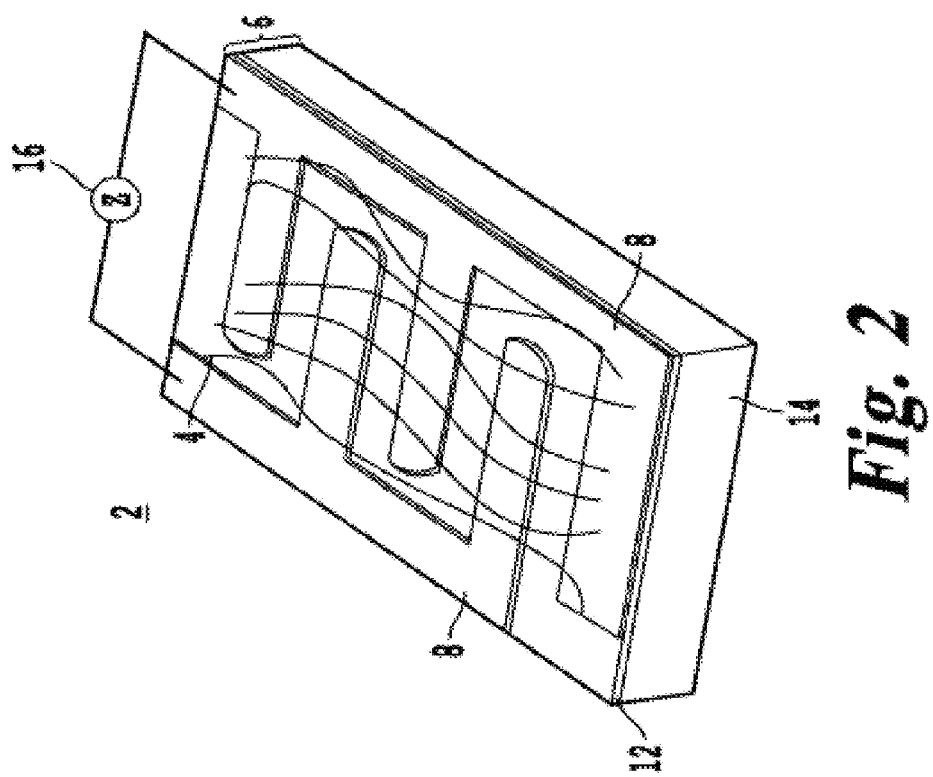
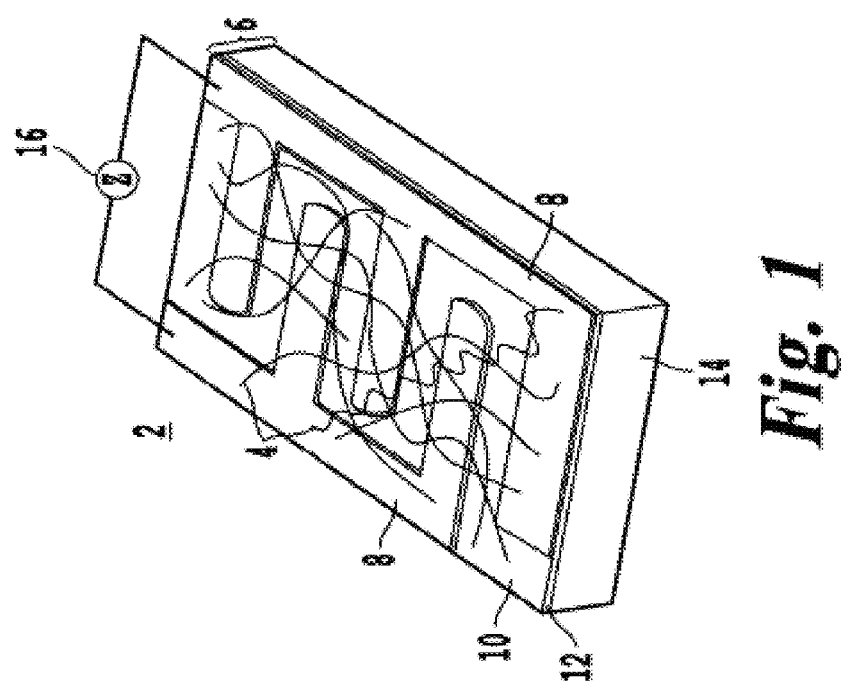

Cross-Sectional View without protective coating with protective coating

ENCASED POLYMER NANOFIBER-BASED ELECTRONIC NOSE

CROSS REFERENCE TO RELATED APPLICATIONS

This application is related to and claims priority to U.S. application Ser. No. 16/580,683, filed on Sep. 24, 2019, entitled "AN ENCASED POLYMER NANOFIBER BASED ELECTRONIC NOSE," the entire contents of which are incorporated herein by reference. This application is related to and claims priority to U.S. application Ser. No. 14/654,292, filed on Jun. 19, 2015, entitled "AN ENCASED POLYMER NANOFIBER BASED ELECTRONIC NOSE," the entire contents of which are incorporated herein by reference. This application is related to and claims priority to PCT/US2013/076052, filed on Dec. 18, 2013, entitled "AN ENCASED POLYMER NANOFIBER BASED ELECTRONIC NOSE." This application is related to and claims priority to U.S. Ser. No. 61/745,023 filed on Dec. 21, 2012, entitled "AN ENCASED POLYMER NANOFIBER BASED ELECTRONIC NOSE." This application is related to U.S. application Ser. No. 11/615,285, filed on Dec. 22, 2006, entitled "POLYMER NANOFIBER-BASED ELECTRONIC NOSE," the entire contents of which are incorporated herein by reference. This application is related to U.S. application Ser. No. 10/819,916, filed on Apr. 8, 2004, entitled "Electrospinning of Polymer Nanofibers Using a Rotating Spray Head," the entire contents of which are incorporated herein by reference. This application is also related to U.S. application Ser. No. 10/819,942, filed on Apr. 8, 2004, entitled "Electrospray/electrospinning Apparatus and Method," the entire contents of which are incorporated herein by reference. This application is related to U.S. application Ser. No. 10/819,945, filed Apr. 8, 2004, entitled "Electrospinning in a Controlled Gaseous Environment," the entire contents of which are incorporated herein by reference. This application is related to U.S. application Ser. No. 11/559,282, filed on Nov. 13, 2006, entitled "Particle Filter System Incorporating Nanofibers," the entire contents of which are incorporated herein by reference. This application is related to U.S. application Ser. No. 11/670,774, filed on Feb. 2, 2007, entitled "A Thermal Preconcentrator for Collection of Chemical Species," the entire contents of which are incorporated herein by reference.

STATEMENT REGARDING FEDERALLY SPONSORED RESEARCH OR DEVELOPMENT

This invention was made with government support under (Contract No. W911QY-10-C-0169) awarded by (Natick Solder Research, Development and Engineering Center). The government has certain rights in the invention.

BACKGROUND OF THE INVENTION

Field of the Invention

The present invention relates to the field of artificial devices known as electronic noses for detecting chemical species.

Description of the Related Art

An electronic nose typically includes two components, an array of chemical sensors and a pattern-recognizer. The array "sniffs" vapors from a sample and provides a set of measurements; the pattern-recognizer compares the pattern of the measurements to stored patterns for known chemical species for identification of the sniffed vapor. Gas sensors tend to have very broad selectivity, and respond differently to different chemical species. This is a disadvantage in many applications, but in the electronic nose, it is utilized as an advantage. Although every sensor in an array may respond to a given chemical, these responses will usually be different. The pattern recognizer evaluates the responses and through predetermined, programmed, or learned patterns ascertains the chemical species affect on the gas sensor.

Recently, attention has been directed to chemically resistive microsensors, which are based on a polymer approach employing insulating polymers and conducting carbon black. In these microsensors, no individual sensor is highly selective toward an individual analyte or chemical species. Some works have shown that chemically sensitive resistors, formed from composites of carbon black with insulating organic polymers, are broadly responsive to a variety of odors. The classification and identification of organic vapors are made through the application of pattern recognition methods. So, the resistance change of sensors can be measured to obtain information about organic gases, as the sensors are exposed to gases.

Among the various electrodes, interdigitated microelectrode arrays have been used where particularly low detection limits are needed. These arrays show higher sensitivities than the conventional electrodes, such as circle electrodes in the area of the gas sensors. Yet, these sensors as reported in the literature have fairly slow response times (e.g., 10 s for detecting concentrations of 400 to 2000 ppm).

The electronic nose can match complex samples with subjective endpoints such as odor or flavor, determining for example when milk has turned sour or when a batch of coffee beans optimally roasted. For instance, the electronic nose can match a set of sensor responses to a calibration set produced by the human taste panel or olfactory panel routinely used in food science. The electronic nose can be used as a production tool to maintain quality over long periods of time.

Several commercial electronic-nose type sensors available are based on either metal oxide or intrinsically-conducting polymers (ICP) as the sensor element. The ones based on polymers include AromaScanϑ, Bloodhoundϑ, AlphaMOSϑ and Zellwegerϑ analytics devices. Specifically, the AromaScanϑ electronic nose, for example, has 32 different sensors in its array, each of which will in general exhibit a specific change in electrical resistance when exposed to air containing an odor. The selective interaction of odors with the sensors produces a pattern of resistance changes for each odor. If an odor is composed of many chemicals, the pattern will be the result of their combined interactions with all of the sensors in the array. It has also been found that the response of the array to varying concentrations of the same odor is non-linear.

In many of the commercial electronic nose sensors, polypyrrole (with different counter ions) electrodeposited as a film across a 10-50 micron gap on a gold interdigitated electrode is commonly used in these sensors. These commercial e-noses have been used to detect spoilage of food, growth of microorganisms, and have been used in medical applications.

Polymers that are typically insulators have been used in e-nose applications by using a conductive filler such as carbon black in the fibers. The filler level is controlled to be near the conduction percolation threshold to obtain high-gain sensors. When exposed to a volatile organic compound (VOC), the polymer swells and its resistance is changed. Spin casting of these polymers over an electrode surface is the conventional technique used to fabricate the commercial polymer-based electronic nose sensors. Multicomponent polymer arrays have been used in commercial devices to generate unique patterns or "fingerprints" associated with different VOCs. The Cyrano C 320Ө e-nose system, for instance, uses 32 sensors.

Previously, commercial electronic nose devices used polymer films either electrodeposited or spin-coated on gold electrode assemblies. The response time for these composite assemblies (as given above) is a function determined by the diffusion kinetics of the vapors through polymer film, and is therefore long.

SUMMARY OF THE INVENTION

In one embodiment of the present invention, there is provided a chemical sensor including a plurality of nanofibers whose electrical impedance varies upon exposure to the chemical species, a substrate supporting and electrically isolating the fibers, a set of electrodes connected to the plurality of fibers at spatially separated points to permit the electrical impedance of the plurality of fibers to be measured, and a membrane encasing the fibers and having a thickness ranging from 50 μm to 5.0 mm.

In another embodiment of the present invention, there is provided a system for sensing a chemical species including the above noted chemical sensor, an impedance measuring device coupled to the electrodes and configured to determine an electrical impedance of the plurality of fibers upon vapor analyte exposure, and an computer analyzer configured to identify the chemical species based on a change in the electrical impedance.

In another embodiment of the present invention, there is provided a method for sensing a chemical species which measures with the above noted chemical sensor at least one change in an electrical impedance between spatially separated electrodes connected to a plurality of fibers upon exposure of the fibers to the chemical species, and identifies the chemical species based on the measured change in the electrical impedance.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein:

FIG. 1 is a schematic of a one embodiment of the invention showing a chemical sensor having a plurality of nanofibers as the sensing elements;

FIG. 2 is a schematic of a another embodiment of the invention showing a chemical sensor having a plurality of oriented nanofibers as the sensing elements;

FIG. 6A-1 is a flowchart depicting a method according to one embodiment of the present invention for making the chemical sensors of the present invention;

FIG. 6A-2 is a flowchart depicting another method according to one embodiment of the present invention for making the chemical sensors of the present invention;

DETAILED DESCRIPTION OF THE PREFERRED EMBODIMENTS

Figures 1, 6A:
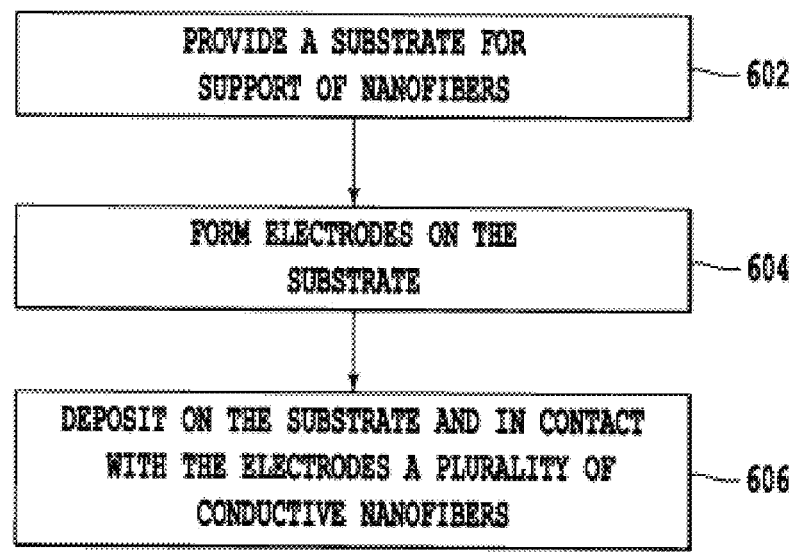

Referring now to the drawings, wherein like reference numerals designate like or corresponding parts throughout the several views, and more particularly to FIG. 1, FIG. 1 depicts chemical sensor 2 of the present invention in which fiber or nano-fiber based materials are used as the active sensing elements. As shown in FIG. 1, the sensing elements include a fiber mat 4 of fibers disposed on a substrate 6. In this embodiment depicted in FIG. 1, the mat of fibers has no preferred orientation. The use of nano-fibers for the fiber mat in one embodiment of the present invention affords high surface area and therefore faster reaction times. The fiber mat 4, in one embodiment of the present invention, includes carbon nanotubes and/or other conducting particles or nanoparticles such as for example gold particles.

As shown in FIG. 1, fibers of the fiber mat 4 are attached to electrodes 8 at longitudinal points of the fibers. The electrodes 8 as shown in FIG. 1 are disposed on an insulating surface 10. The insulating surface 10 in one embodiment of the present invention is an insulator 12 deposited on a silicon wafer 14 containing circuitry 16 to analyze the impedance of the fiber mat and more specifically the change in impedance of the mat of fibers. If an insulating substrate is used instead of wafer 14, insulator 12 may not be required. The circuitry 16 in one embodiment of the present invention includes a temperature sensor such as a platinum resistance element or a thermocouple so that any changes in temperature of the nanofibers are considered as part of the change in impedance, and thereby the change in impedance due to VOC absorption on the nanofibers can be distinguished from a temperature induced change in impedance.

In another embodiment of the present invention, the fibers can be immersed in an aqueous solution and traces of organic solvent present in the aqueous solution will swell the polymer nanofiber and lead to overall conductivity change of the sensing material. Thus, the chemical sensor of the present invention can be used in gaseous and liquid environments.

Figures 2, 6A:
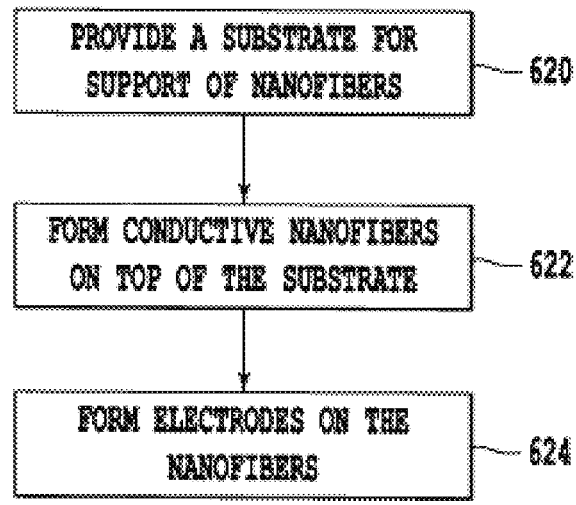

As shown in FIG. 2, in one embodiment of the present invention, the fiber mat 4 can be preferentially oriented (formed for example by methods described below). In this embodiment, the change in impedance is more pronounced than in the configuration shown in FIG. 1 when the fiber mat 4 does not have a preferential alignment. Aligned fibers can help increase the reproducibility of the sensor response. Experience has shown that a higher degree of alignment produces more reproducible sensor responses. As shown in FIGS. 1 and 2, in one embodiment of the present invention, an interdigitated electrode 8 is used. One suitable interdigitated electrode has 15 µm electrode width and 15 µm electrode spacing. Other spacings in the range of 1 µm to 50 µm are also suitable for the present invention.

Figure 3A:
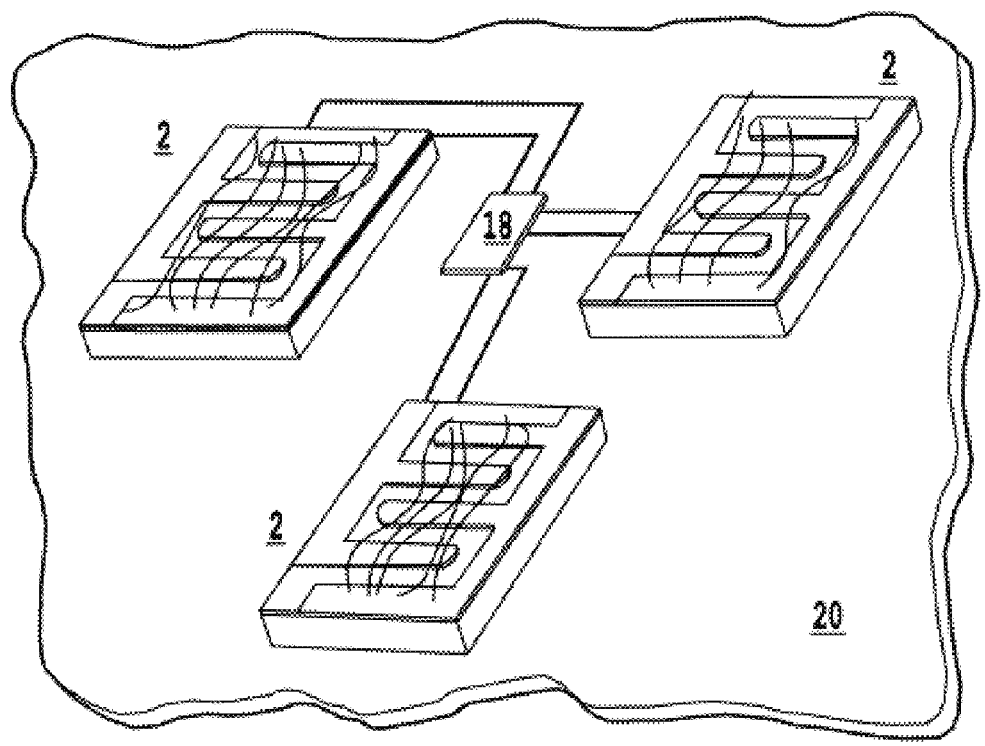
FIG. 3A is a schematic of another embodiment of the invention showing a chemical sensor system utilizing the sensing elements in FIG. 2, integrated onto a silicon device chip, and coupled to an analyzer.

As shown in FIG. 3A, in one embodiment of the present invention, the sensors 2 can be coupled to an analyzer 18, that determines a change of impedance of the nanofibers based on adsorption of a chemical species. The analyzer 18 can be a general purpose computer as described later in relation to FIG. 8. The analyzer 18 is programmed with instructions by which the chemical species inducing the impedance change can be deduced. Further, as shown in FIG. 3A, multiple sensors 2 can be used where the fibers or nanofibers on each sensor 2 preferentially react to a particular chemical species. While shown in FIG. 3A as integrated onto a silicon wafer die 20, the sensors and analyzer 18 can be integrated onto a circuit board.

The adsorbed chemical species swell the polymer composing the fibers or nanofibers which induces a change in the impedance of the composite nanofiber. During a sensing process of the present invention, a set of data on for example resistance variations for the entire array of sensing materials will be obtained and analyzed by a pattern recognition engine. The extracted feature for each individual chemical species will be compared to a database obtained from the massive screening and data collection during validation of the chemical sensor system.

Figure 3B:
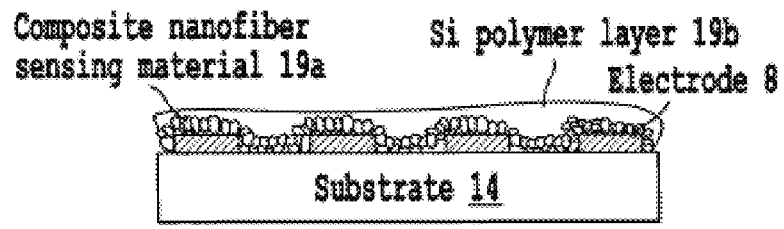
FIG. 3B is a schematic illustration showing a sensor device according to one embodiment of the present invention enveloped in a thin film of silicone rubber or other polymer that sorbs and concentrates VOCs from air.

In one embodiment of the present invention, as shown in FIG. 3B, a sensor device 2 is formed by a sensing material 19a enveloped in a thin film 19b of silicone rubber or other polymer that sorbs and concentrates VOCs from air. The sensing material such as for example the above-described fiber mats is deposited onto interdigitated microelectrode and the interdigitated electrode is connected to a resistance measuring device (not shown here for the sake of simplicity) for data-logging such as for example the analyzer 18 of FIG. 3A. The data in one embodiment of the present invention is transferred by a computer interface. The data is then compared to existing saved databases for identification of the VOC or, if unknown at the time, saved to a sensor response database for future reference.

In the embodiment shown in FIG. 3B, electrodes 8 contact the side of the fiber mat toward the substrate. The thickness of the overcoat layer is between 200 nm-2 µm. A cross-linked polydimethylsiloxane (PDMS) film is suitable for this purpose. As shown in FIG. 3B, the fiber mat 4 is encased between the film 19 and the substrate 14. A high partition coefficient for VOCs (as explained below) will ensure a higher concentration of the ambient VOC in PDMS as opposed to in air. The availability of a concentrated source of the VOC in the silicone matrix, next to the nanofiber-based sensor improves the sensitivity and the detection limit of the sensor device of the present invention. When two phases (in this case ambient air and the silicone polymer) are in contact with each other, at equilibrium a given VOC in air distributes into the two phases. The ratio of their concentrations in the two phases is the partition coefficient. The partition coefficient varies with the nature of the VOC and can assume a variety of values. In one embodiment of the present invention, the concentration of VOC in the vicinity of the silicone encapsulated electrode is increased, as the partition coefficient becomes $\gg 1$.

In one embodiment of the present invention, (n or p doped) intrinsically conducting polymers might also be used. In one embodiment of the present invention, the nanotubes are used as a reinforcing filler in the polymers to improve mechanical integrity. Other conducting materials can also be used as dopants in the polymer nanofiber, such as particles of metal and carbon.

In one embodiment of the present invention, the polymers are conductive polymers that do not necessarily have to be doped. Such polymers include for example polyaniline, polypyrrole, and polythiophene. These polymers typically have a resistivity of $10^{-5}$ Ω-cm or less.

Figure 3C:
FIG. 3C is a schematic diagram showing the inclusion of carbon nanotubes in a sensor fiber of the present invention.

In one embodiment of the present invention, carbon nanotubes (SWCN) or multi-wall carbon nanotubes (MWCN) are used to affect the conductivity of the fibers. For example, the use of 1-30 weight percent of the single wall carbon nanotubes (SWCN) or the multi-wall carbon nanotubes (MWCN) changes the electrical resistivity of conventional polymers such as polycarbonates, acrylic polymers or polysulfone. Indeed, concentrations of SWCN or MWCN within 10% of the conduction percolation threshold are suitable for the present invention. Carbon nanotubes can be used at levels that are at or considerably above or below this threshold. FIG. 3C is a schematic diagram showing the inclusion of carbon nanotubes in a sensor fiber of the present invention. From this figure, it can be seen that expansion of the fiber polymer would increase the separation distance between the carbon nanotubes and increase the impedance of the fiber to electrical conduction.

A suitable electrode in one embodiment of the present invention is an interdigitated electrode 8 having for example a gap of 50 microns. Gold is a suitable electrode material, but other electrodes such as Ag, Cu, Al, W, Ta, and Tn can be used. Any conducting metal can be used the electrode materials.

Additionally, in one embodiment of the present invention the electrodes can be formed by a printing process. Instead of the preformed inter-digitated gold electrodes discussed above, printed electrodes are used. In this embodiment, a set of electrodes of a suitable geometry are printed using a chemical printer or a modified inkjet printer loaded with a conducting ink. The electrodes can be printed on top of (or below) a composite fiber or nanofiber (polymer+carbon nanotubes) mat that is generated on top of a glass or non-conducting material. The geometry may or may not be interdigitated and the distance between electrodes can be varied according to the present invention. This approach permits low-cost fabrication of sensors and their application on textile or other surfaces. Other printing methods (such as screen printing) can be used according to the present invention.

Figure 3D:
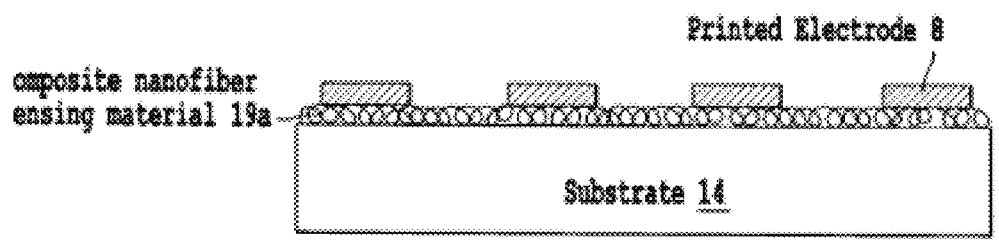
FIG. 3D is a schematic illustration showing according to one embodiment of the present invention a chemical sensor having printed electrodes on the top of the electrospun nanofiber sensing material.

FIG. 3D is a schematic illustration showing, according to one embodiment of the present invention, a chemical sensor 2 having printed electrodes 8. In this embodiment of the present invention, the printed electrodes 8 are formed on the fiber mat 19a at designated positions above for example a glass or quartz substrate 14.

Alternatively, in one embodiment of the present invention, the electrodes are formed on top of a mat of pre-spun fibers. Besides printing, sputter coating could be used to deposit electrode materials through a shadow mask to produce a desired electrode pattern on the fiber mat.

Whether by ink jet printing, screen printing, or sputtering or other known processes for electrode patterning, medium such as for example fabric, paper, plastic, ceramic or other material may have electrodes placed on one or both surfaces of the medium and in turn placed in contact with the fiber mat.

Figure 3E:
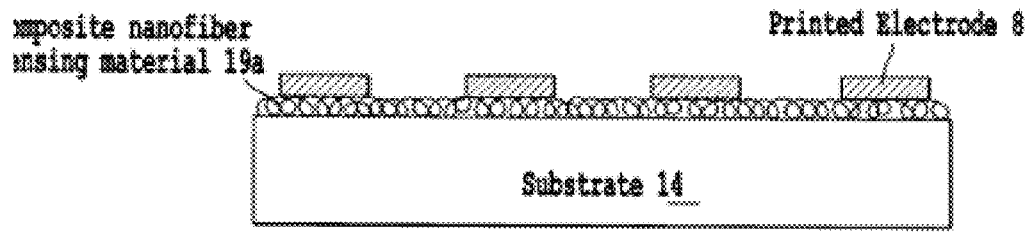
FIG. 3E is a schematic illustration showing according to one embodiment of the present invention a chemical sensor having printed electrodes on the top of the electrospun nanofiber sensing material with a covering membrane.
Figure 3E:

FIG. 3E is a schematic illustration showing, according to one embodiment of the present invention, a chemical sensor 2 having printed electrodes 8. In this embodiment of the present invention, the printed electrodes 8 are formed on the fiber mat 19A at designated positions above for example a glass or quartz substrate 12 or other substrates mentioned above. A membrane 19c is positioned directly on the electrodes 8 to provide physical protection, support for droplets during measurement and act as a concentrating material by the virtue of selective partitioning of various materials. Membrane 19c could bridge the space between electrodes as depicted or could conformally cover the electrodes and the fibers. Membrane 19c could be permeable or semi-permeable monoliths or fibrous mats or textiles, flexible and non-flexible materials, and composed of a range of materials including for example silicone or polycarbonate polymers, and ceramics. Further the substrate 14 could be made of a comparable range of materials. The membrane material can be made with polymeric membranes and/or layer of fibers or electrospun polymer nanofibers. The polymeric membrane material can be used by present invention, but are not limited to, silicones, cellulose acetate, nitrocellulose, and cellulose esters (CA, CN, and CE), polysulfone (PS), polyether sulfone(PES), polyacrilonitrile (PAN), polyamide, polyimide, polyethylene and polypropylene (PE and PP), polytetrafluoroethylene (PTFE), polyvinylidene fluoride (PVDF), and polyvinylchloride (PVC).

The fibers or nanofibers produced by the present invention include, but are not limited to, acrylonitrile/butadiene copolymer, cellulose, cellulose acetate, chitosan, collagen, DNA, fibrinogen, fibronectin, nylon, poly(acrylic acid), poly (chloro styrene), poly(dimethyl siloxane), poly(ether imide), poly(ether sulfone), poly(ethyl acrylate), poly(ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly(vinylpyrrolidone), proteins, SEBS copolymer, silk, and styrene/isoprene copolymer.

Additionally, fibers made by polymer blends can also be produced as long as the two or more polymers are soluble in a common solvent. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly (methyl methacrylate), poly(hydroxystyrene)-blend-poly (ethylene oxide)).

In one embodiment of the present invention, nanofiber sensing elements are directly electrospun from sonicated solutions of the carbon nanotubes (CNT) and polymer material onto an appropriate electrode system maintained at a ground potential or at a high potential of opposite polarity from the electrospinning units.

A polymer solution in dimethylformamide (DMF) containing 20 percent (w/w) of polymethyl-methacrylate (PMMA) polymer and 10% (w/w on polymer) of single wall carbon nanotubes (SWCNT) sonicated for a period of 8 hours is, according to the present invention, a suitable electrospinning solution by which to electrospin the nanofibers. Such a solution may be electrospun for example in the apparatus described in U.S. application Ser. No. 10/819,945, filed Apr. 8, 2004, entitled "Electrospinning in a Controlled Gaseous Environment," the entire contents of which are incorporated herein by reference.

Figure 4:
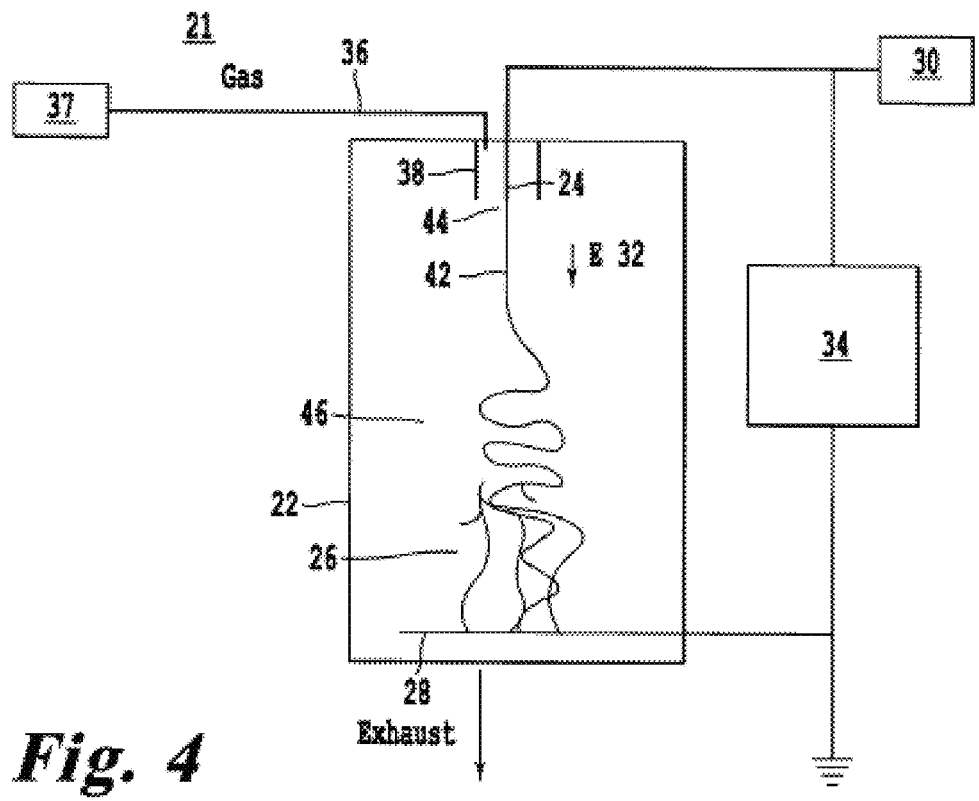
FIG. 4 is a schematic illustration depicting an electrospinning apparatus suitable for deposition of fibers and nano-fibers of the present invention.

FIG. 4 is a schematic illustration depicting an electrospinning apparatus suitable for deposition of nanofibers of the present invention. FIG. 4 is a schematic illustration of an electrospinning apparatus 21 according to one embodiment the present invention in which a chamber 22 surrounds an electrospinning electrospinning element 24. As such, the electrospinning element 24 is configured to electrospin a substance from which fibers are composed to form fibers 26. The electrospinning apparatus 21 includes a collector 28 disposed from the electrospinning element 24 and configured to collect the fibers.

The electrospinning element 24 communicates with a reservoir supply 30 containing the electrospinning medium such as for example the above-noted polymer solution. The electrospinning medium of the present invention includes polymer solutions and/or melts known in the art for the extrusion of fibers including extrusions of nanofiber materials. Indeed, polymers and solvents suitable for the present invention include for example polystyrene in dimethylformamide or toluene, polycaprolactone in dimethylformamide/methylene chloride mixture (20/80 w/w), poly(ethyleneoxide) in distilled water, poly(acrylic acid) in distilled water, poly(methyl methacrylate) PMMA in acetone, cellulose acetate in acetone, polyacrylonitrile in dimethylformamide, polylactide in dichloromethane or dimethylformamide, and poly(vinylalcohol) in distilled water. Thus, in general, suitable solvents for the present invention include both organic and inorganic solvents in which polymers can be dissolved.

A high voltage source 34 is provided to maintain the electrospinning element 24 at a high voltage. The collector 28 is placed preferably 1 to 100 cm away from the tip of the electrospinning element 24. The collector 28 can be a plate or a screen. Typically, an electric field strength between 2,000 and 400,000 V/m is established by the high voltage source 34. The high voltage source 34 is preferably a DC source, such as for example Bertan Model 105-20R (Bertan, Valhalla, N.Y.) or for example Gamma High Voltage Research Model ES30P (Gamma High Voltage Research Inc., Ormond Beach, Fla.). Typically, the collector 28 is grounded, and the fibers 26 produced by electrospinning from the electrospinning elements 24 are directed by the electric field 32 toward the collector 28.

With reference to FIG. 4, the electric field 32 pulls the substance from which the fiber is to be composed as a filament or liquid jet 42 of fluid from the tip of the electrospinning element 24. A supply of the substance to each electrospinning element 24 is preferably balanced with the electric field strength responsible for extracting the substance from which the fibers are to be composed so that a droplet shape exiting the electrospinning element 24 is maintained constant.

As illustrative of the electrospinning process of the present invention, the following non-limiting example is given to illustrate selection of the polymer, solvent, a gap distance between a tip of the electrospinning element and the collection surface, solvent pump rate, and addition of electronegative gases:

a polystyrene solution of a molecular weight of 350 kg/mol,
 a solvent of dimethylformamide DMF,
 an electrospinning element tip diameter of 1000 μm,
 an Al plate collector,
 ~0.5 ml/hr pump rate providing the polymer solution,
 an electronegative gas flow of $CO_2$ at 8 lpm,
 an electric field strength of 2 KV/cm,
and a gap distance between the tip of the electrospinning element and the collector of 17.5 cm.

Furthermore, as illustrated above in FIG. 2, in one embodiment of the present invention oriented nanofibers are produced. To obtain aligned nanofibers, both electrodes might be grounded or held at a potential of opposite polarity (relatively to the spinhead). Further, techniques as described in U.S. application Ser. No. 10/819,916, filed on Apr. 8, 2004, entitled "Electrospinning of Polymer Nanofibers Using a Rotating Spray Head," the entire contents of which are incorporated herein by reference, can be used in the present invention to produce oriented fibers.

Figure 5A:
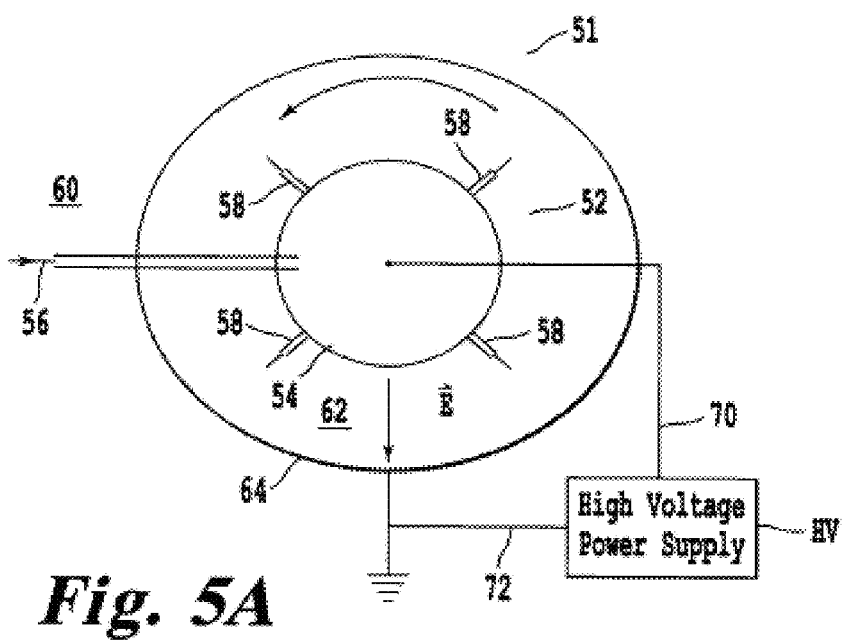
FIG. 5A is a schematic illustration showing a top view of an electrospinning apparatus 21 of one embodiment of the present invention for electrospinning oriented conducting fibers and nano-fibers.
Figure 5B:
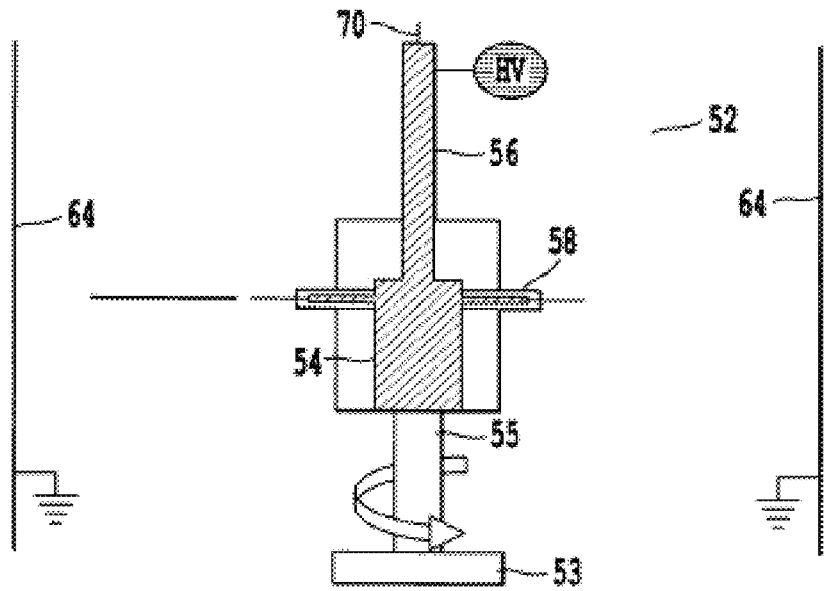
FIG. 5B is a schematic illustration showing a side view of an electrospinning apparatus in FIG. 5B.

FIG. 5A is a schematic illustration showing a top view of an electrospinning apparatus 51 for electrospinning oriented conducting nanofibers. FIG. 5A depicts a rotatable spray head 52 including a reservoir 54 holding a substance from which the fibers are to be extruded. FIG. 5B shows a side view of the electrospinning apparatus 51. In FIG. 5B, the electrospray medium is shown illustratively being feed to the reservoir 54 along an axial direction of the electrospinning apparatus 51. The electrospinning medium 56 is electrospun from a plurality of electrospinning elements 58. The rotatable spray head 52 is preferably rotated about its center, and the spray of the electrospinning medium 56 occurs radially from the electrospinning elements 58 placed on the periphery of the rotatable spray head 52. The rotatable spray head 52 is preferably a cylindrical structure, but other structures such as for example polygonal structures are suitable. The rotatable spray head 52 includes a passage 60 for supplying the electrospinning medium 56 to the reservoir 54.

An electric potential applied to the rotatable spray head 52 establishes an electric field 62 as shown in FIG. 5A which extends to a collector 64 constituting an opposite electrode. The geometrical arrangement of the rotatable spray head 52 and the collector 64 configures the electric field strength and distribution. An electric field strength of about 3 kV/cm in the present invention is preferred. In the present invention, the spray head 52 constitutes an electrifiable chamber (i.e., a chamber upon which an electric potential can be established). The electrospinning medium 56 upon extraction from a tip of the plural electrospinning elements 58 is guided along a direction of the electric field 52 toward the collector 64, but is deflected according to the centrifugal forces on the electrospun fibers.

The rotatable spray head 52, shown for example in FIG. 5A, can be a cylindrical vessel. On spinning, the electrospinning medium 56 being a viscous solution is forced into the electrospinning elements 58. The electric field 62 existing about the rotatable spray head 52 then extracts the electrospinning medium 56 from the reservoir 54 to a tip end of the electrospinning elements 58. The extracted medium 56 dries in the ambient about the rotatable spray head 52 to form fibers.

Upon extrusion from the rotatable spray head 52, the electrospun fibers collect on the collector 64. The collected fibers are deposited on the surface of the collector 64 with a degree of orientation dependent on the speed of rotation, the electric potential of the rotatable spray head 52, and the viscosity of the solution. According to the present invention, the fiber characteristics as well as the orientation can be controlled by the centrifugal forces generated by the spinning of the rotatable spray head 22 to be discussed below.

The electric field 62 is produced between the rotatable spray head 52 and the collector by applying a high voltage power source HV, as shown in FIG. 5A. The high voltage power source HV can be commercial power source, such as for example Bertan Model 105-20R (Bertan, Valhalla, N.Y.) or for example Gamma High Voltage Research Model ES30P (Gamma High Voltage Research Inc., Ormond Beach, Fla.). Typically, an electric field strength between 2,000 and 400,000 V/m is established by the high voltage source.

The collector 64 can be grounded, and the fibers produced by electrospinning are directed by the electric field 62 toward the collector 64. The electrospun fibers are deposited on the collector 64, accumulate thereon, and are subsequently removed. A rotating mechanism (not shown) rotates the rotatable spray head 62 at a preset angular speed. An angular rotation speed of 500-10,000 rpm is preferred.

Electrospinning of polymer solutions containing carbon nanotubes (single or multi walled) is similar to the electrospinning polymers without the nanotubes. However, care must be taken to sonicate the carbon nanotubes in solvent prior to mixing with the polymer to ensure adequate dispersion. Adequate dispersion results in uniform conductivity as well as the ability to reach a percolation threshold at low concentrations of the conducting filler material. Normally, a sonication time greater than 24 hours is sufficient to obtain a uniform carbon nanotube suspension in the solution. Normally <5% of carbon nanotubes will make the percolation threshold; however, this value of carbon nanotube concentration depends on the length of the carbon nanotubes and purity of the carbon nanotubes. Accordingly, concentrations of carbon nanotubes suitable for the present invention in those embodiments at the percolation threshold range from 1% to 30%. In other embodiments, weight concentrations as low as 0.5% have been shown to be responsive. In other embodiments, the weight concentrations are less than 5%.

FIG. 6A-1 is a schematic depicting a flowchart according to a method of the present invention. As depicted in FIG. 6A-1, one method of the present invention includes in step 602 providing a substrate for support of nanofibers. The method includes in step 604 depositing electrodes on the substrate. The method includes in step 606 depositing on the substrate and contacting the electrodes a plurality of conductive gas-absorbing nanofibers whose electrical resistance varies upon exposure to a chemical compound.

In step 606, the method preferably electrospins the substance in an electric field strength of 2,000-400,000 V/m although as noted above other techniques can be used. The fibers or nanofibers produced by the present invention include, but are not limited to, acrylonitrile/butadiene copolymer, cellulose, cellulose acetate, chitosan, collagen, DNA, fibrinogen, fibronectin, nylon, poly(acrylic acid), poly (chloro styrene), poly(dimethyl siloxane), poly(ether imide), poly(ether sulfone), poly(ethyl acrylate), poly(ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly(vinylpyrrolidone), proteins, SEBS copolymer, silk, and styrene/isoprene copolymer.

Additionally, polymer blends can also be produced as long as the two or more polymers are soluble in a common solvent. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly(methyl methacrylate), poly(hydroxystyrene)-blend-poly(ethylene oxide)).

The fibers deposited in the one embodiment of the present invention may range from 50 nm to several microns in diameter and may contain amounts of carbon nanotubes or other conductive filler varying from a fraction of a percent to 0.5 or 30 percent by weight. Besides, carbon nanotubes, dopants such as metallic particles can be used to permit the deposited nanofibers to be electrically conductive.

FIG. 6A-2 is a schematic depicting a flowchart according to another method of the present invention. As depicted in FIG. 6A-2, one method of the present invention includes in step 620 providing a substrate for support of nanofibers. The method includes in step 622 forms on the substrate conductive gas-absorbing nanofibers whose electrical resistance varies upon exposure to a chemical compound. The method includes in step 624 depositing on the fibers electrodes to make contact to the conductive gas-absorbing nanofibers.

In step 622, the method preferably electrospins the substance in an electric field strength of 2,000-400,000 V/m although as noted above other techniques can be used. The fibers or nanofibers produced by the present invention include, but are not limited to, acrylonitrile/butadiene copolymer, cellulose, cellulose acetate, chitosan, collagen, DNA, fibrinogen, fibronectin, nylon, poly(acrylic acid), poly (chloro styrene), poly(dimethyl siloxane), poly(ether imide), poly(ether sulfone), poly(ethyl acrylate), poly(ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly(vinylpyrrolidone), proteins, SEBS copolymer, silk, and styrene/isoprene copolymer.

Additionally, as before, polymer blends can also be produced as long as the two or more polymers are soluble in a common solvent. A few examples would be: poly(vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly(methyl methacrylate), poly(hydroxystyrene)-blend-poly(ethylene oxide)).

As before, the fibers deposited in this embodiment of the present invention may range from 50 nm to several microns in diameter and may contain amounts of carbon nanotubes or other conductive filler varying from a fraction of a percent to 0.5 or 30 percent by weight. Besides, carbon nanotubes, dopants such as metallic particles can be used to permit the deposited nanofibers to be electrically conductive.

Further refinements of the electrospinning process are described in U.S. application Ser. No. 11/559,282, filed on Nov. 13, 2006, entitled "Particle Filter System Incorporating Nanofibers," previously incorporated herein by reference. The practices described there can be used in the present invention to produce small diameter nanofibers whose large surface to volume ratio will enhance the sorption of chemical species in the various chemical sensors of the present invention.

In one embodiment of the present invention, stainless steel extrusion tips having internal diameters (ID) from 0.15 to 0.58 mm are used. In another refinement, polytetrafluoroethane (i.e., Teflon) capillary tubes with ID from 0.07-0.30 mm are used. Both types of orifices can produce submicron fibers. For both orifices, low flow rates coupled with high voltage drops typically resulted in the smallest fiber diameters (e.g, <200 nm). In both cases, the voltage was 22 kV to 30 kV for a 17.8-25.4 cm gap (i.e., the distance between tip 16 and electrode 20). In one embodiment of the present invention, the voltage per gap is a parameter providing pulling strength for the electrospinning. The gap in part determines travel time of the electrospun fiber to the collector, and thus determines stretching and solvent evaporation times. In one embodiment of the present invention, different $CO_2$ purge flow rates around needle 18 (i.e., as a gas jacket flow around and over the tip 16 in the fiber pull direction) for the different spinning orifices are utilized to improve the electrospun fibers.

When stainless steel needles were used, higher gas flow rates of $CO_2$ (e.g., increasing from 8 lpm to 13 lpm) typically resulted in improved fibers with smaller diameters. Reductions of 30 to 100 nm in AFD were observed, permitting (in most cases) fibers with AHD less than 200 nm to be achieved by these methods of the present invention.

In contrast, when Teflon capillary tubes were used, the fiber quality was usually degraded with increasing $CO_2$ flow rate from 8 lpm to 13 lpm. The number of beads and other fiber defects increased. For Teflon capillary tube, a flow rate of about 8 lpm is suitable for small (less than 200 nm) diameter fibers, whereas a higher flow rate is suitable for stainless steel capillary tubes. The values for electronegative gas flow rates (in this case $CO_2$) given here are only examples, other gas flow rates may be used given the combination of electrospinning orifice, polymer formulation, and electrospinning conditions used in order to obtain small diameter nanofibers.

In one embodiment of the present invention, the relative humidity RH of the electrospinning chamber also effects fiber morphology. In one example, using 21 wt % PSu in DMAC, a high RH>65%, resulted in fibers that had very few defects and smooth surfaces but larger diameters, as compared to electrospun fibers produces at RH>65%. Low RH<13%, resulted in smaller fibers but having more defects (e.g., deviations from smooth round fibers). Modestly low RH, 40% to 22%, typically produced a small fiber size with fewer defects.

A variety of mechanisms to control the chamber RH are available, according to various embodiments of the present invention, from placing materials that absorb (e.g. calcium sulfate) or emit water moisture (e.g., hydrogels) in the electrospinning chamber, operating a small humidifier in the chamber, or other ways of introducing moisture into the electrospinning chamber. For example, suitable results were obtained by bubbling $CO_2$ through deionized water and then introducing the humidified gas into the chamber. Two gas streams (one humidified and one dry) can be used to obtain a desired RH for the chamber and/or for the gas jacket flowing over the electrospinning orifice.

Thus, in one example of the present invention, a combination of a Teflon capillary tube, an 8 lpm $CO_2$ purge rate, under a RH of 30%, using PSu in DMAC produced nanofibers with an AFD of less than 100 nm. While a combination of a stainless steel capillary tube, a 13 lpm $CO_2$ purge rate, under a RH of 30%, using PSu in DMAC produced nanofibers with an AFD of less than 100 nm.

In another example of the present invention, nanofibers were electrospun with a solution of 21 wt % PSu in N,N-dimethylacetamide (DMAC), with the solution containing 0.2 wt. % of the surfactant tetra butyl ammonium chloride (TBAC). The surfactant lowers the surface tension and raises the ionic conductivity and dielectric constant of the solution. The polymer solution was spun from a 30G (ID 0.154 mm) stainless steel needle with a flow rate of 0.05 ml/hr, a gap of 25 cm between the needle and target, an applied potential of 29.5 kV DC, a $CO_2$ gas jacket flow rate of 6.5 lpm, and an RH in the range of 22 to 38%. Inspection by SEM indicated an average fiber diameter (AFD) of 82±35 nm with the smallest observed fibers being in the 30 to 40 nm range.

In another example, polycarbonate PC can be spun from a 15 wt % solution of polymer in a 50/50 solution of tetrahydrofuran (THF) and N,N-dimethyl formamide (DMF) with 0.06 wt % TBAC. A 30 gauge stainless steel needle, a polymer solution flow rate of 0.5 ml/hr, and a $CO_2$ flow rate of 8 lpm were used with a gap of 25.4 cm and applied potential of 25 kV to obtain sub 200 nm fibers. Inspection by SEM indicated an AFD of 150±31 nm with the smallest fibers being around 100 nm.

While described here are a number of examples of electrospun fiber formation processes, this invention is not limited to electrospinning Other techniques for forming nanofibers such as electroblowing or melt blowing can be used here in the present invention. The polymers utilized may be intrinsic semiconductors or an insulating polymer filled with conducting particles selected to provide desired properties at the electrical percolation point. The terms "electroblowing" and "electro-blown spinning" are used in the art to refer interchangeably to a process for forming a fibrous web by which a forwarding gas stream is directed generally towards a collector, into which gas stream a polymer stream is injected from a spinning nozzle, thereby forming a fibrous web which is collected on the collector, wherein a voltage differential is maintained between the spinning nozzle and an electrode and the voltage differential is of sufficient strength to impart charge on the polymer as it issues from the spinning nozzle.

Such techniques are described in U.S. Pat. No. 7,931,456 (the entire contents of which are incorporated herein by reference). Using that technique for example, nanofibers suitable for this invention can be formed by an electroblowing process which issues an electrically charged polymer stream from a spinning nozzle in a spinneret and which passes the polymer stream by an electrode to which a voltage is applied. The spinneret is substantially grounded, such that an electric field is generated between the spinneret and the electrode of sufficient strength to impart electrical charge to the polymer stream as it issues from the spinning nozzle. Finally, with this method, the nanofibers formed from the charged polymer stream could be deposited on a collector holding for example the substrates described above with inter-digitated electrodes. Alternatively, with this method, the nanofibers formed from the charged polymer stream could be deposited on a collector holding for example the substrates without electrodes or used to form a mat of suitable thickness in a roll-to-roll format that could be cut into the appropriate size, and placed on a support. In that case, the electrodes would be later added to the deposited fibers to form the sensors of this invention. With these alternative techniques to electrospinning, fibers larger than 500 nm in diameter can be produced. These fibers while still expected to be responsive may not be as responsive as fibers less than 1000 nm in size, as the surface area of the material dramatically increases with decreased nanofiber diameter in nanometer size range influencing sensitivity and the response time governed by the diffusion time of the chemicals to penetrate the cross-section of the fiber.

Work has shown that direct electrospinning of nanofibers on gold electrodes may not always result in adequate electrical contact between the nanofibers and metal to allow the sensor to function satisfactorily. To address this shortcoming, in one embodiment of the present invention, a spincoat of a bonding polymer such as propylene glycol monomethyl ether (PGME) is applied prior to electrospinning the fibers or nano-fibers to promote electrical contact to an underlying conductive substrate such as for example a gold or gold plated substrate. Other polymers that have appropriate functional groups capable of non-bonded interaction with the fiber mat might also be used in place of PGME.

In another embodiment of the present invention, electrical contact between an electrode and a conductive filler (or additive) in the nanofiber such as carbon nanotubes is enhanced by treating the nanofiber/electrode assembly to promote local enhancement in the conductivity between the conductive filler and the electrode. For example, in one illustration, the electrodes are heated to locally deform the nanofibers, thereby promoting better electrical contact between nanofibers and electrode.

Alternatively, the electrical connection can be improved (as detailed before) by printing electrode with a conductive ink including a solvent for the fibers.

Once the fibers or nanofibers have been electrospun, the chemical sensor is thoroughly dried to remove residual spinning solvents and is connected via the electrode terminals to a recording meter included for example in the circuitry 16 or in the analyzer 18 to read the impedance across the electrodes. For example, the change can be reported as dimensionless resistance change $\Delta(\overline{R}/R)$. This quantity changes with the amount of VOC in the immediate environment of the sensor. This technology relies on pattern recognition applied to empirical sensor array resistance data to distinguish one VOC from another. As in conventional E-nose systems, each VOC of interest will essentially have a 'fingerprint' in terms of its effect on the individual sensor elements.

Figure 6B:
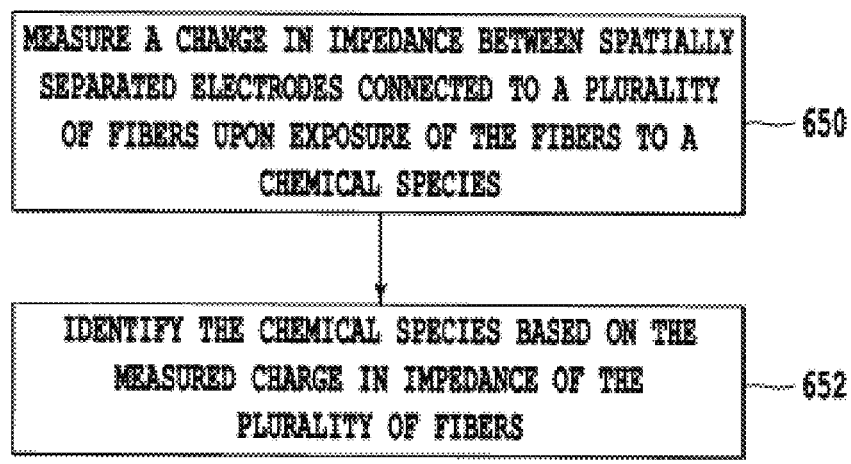
FIG. 6B is a flowchart depicting a method according to one embodiment of the present invention for sensing a chemical species.

FIG. 6B is a schematic depicting a flowchart according to a method of the present invention for identifying a chemical species (e.g., an airborne chemical species). At 650, a change in electrical impedance (e.g., capacitance, inductance, or resistance) between spatially separated electrodes connected to a plurality of fibers upon exposure of the fibers to the chemical species. At 652, the chemical species is identified based on the change in the electrical impedance of the plurality of fibers.

At 650, the change in electrical impedance can be measured for a plurality of nanofibers whose average fiber diameter is preferably less than 500 nm or more preferably less than 100 nm, although as noted above larger diameter fibers can be used. The change in electrical impedance can be measured for a plurality of conductive fibers. The conductive fibers can have a non-conducting medium and a conducting medium such that a density of the conducting medium in the fibers permits electrical conduction by percolation of charge carriers between regions of the conducting medium.

At 652, the chemical species can be identified by comparing the measured change to a library of changes for known concentrations of predetermined chemical species or by comparing measured changes for a plurality of different fibers to a library of changes for known concentrations of different predetermined chemical species.

Figure 7A:
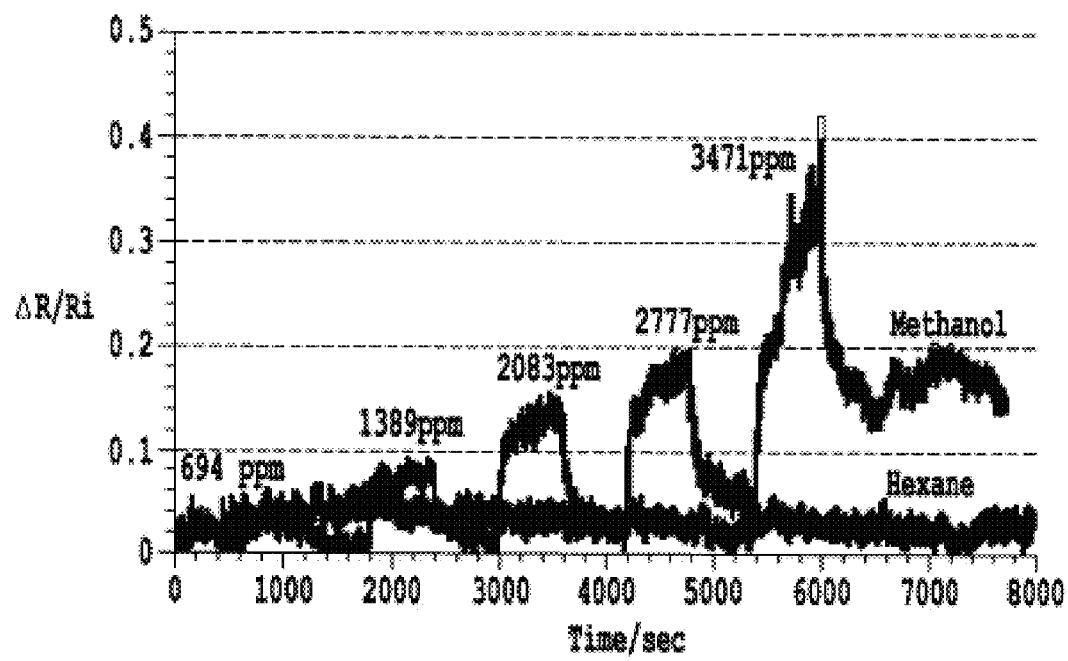
FIGS. 7A and 7B are graphs showing a typical response of the chemical sensor of the present invention.
Figure 7B:
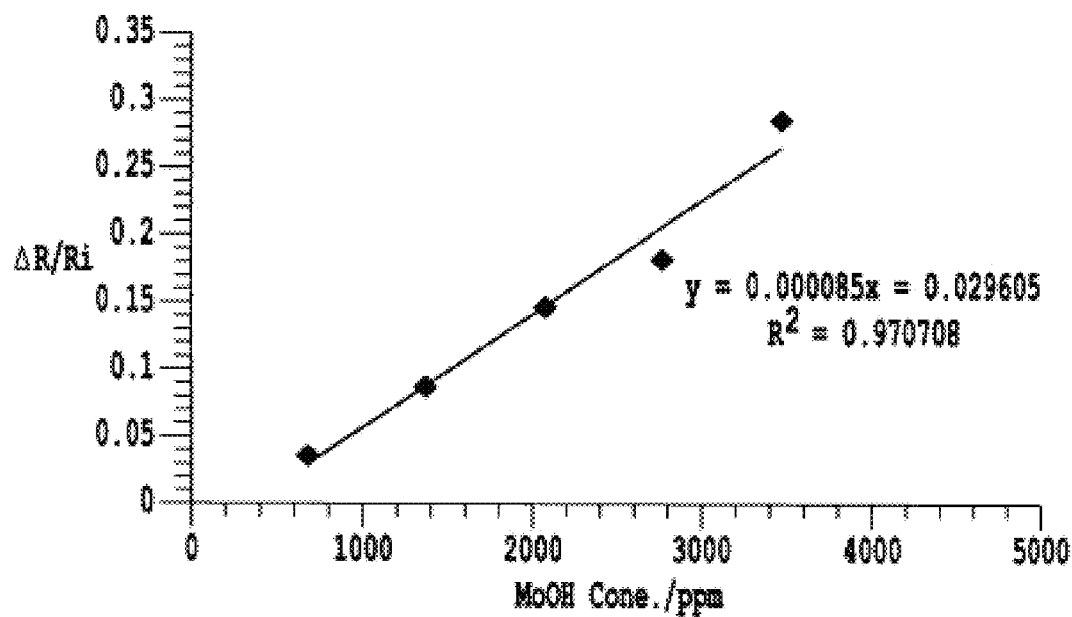

FIGS. 7A and 7B are graphs showing a typical response of the chemical sensor of the present invention. FIG. 7A specifically shows a response profile of a fiber mat of PMMA+8% SWCNTS to methanol (MeOH) and hexane (Hx). These results indicate that a response time for the nanofiber sensor of the present invention (from baseline to resistance increase) is less than 30 seconds. FIG. 7A specifically shows the high selectivity of the polymer and SWCNTs composite nanofiber sensor of the present invention, as the response methanol is many times more sensitive than the response to hexane. FIG. 7B specifically shows the relative differential resistance change $\Delta R/R_i$ Vs for a methanol vapor concentration.

The use of nanofibers in the present invention is particularly beneficial in that it increases the sensitivity and decreases the response time of the sensor due to the high surface area of the fibers and the very small diffusion path (these effects are enhanced if nanofibers are used). The use of nanofibers is cost effective due to the low cost and small quantity of materials when nanofibers are used. Further, the use of nanofibers facilitates miniaturization of the sensor system due to the high sensitivity of nanofibers owing to their high surface area. Also unlike polymer films, the nanofiber mats of the present invention are permeable to gases and their use can allow sensors that can be incorporated into filters.

Measured results have shown the ability of the sensors of the present invention to respond rapidly to changing concentrations of a VOC in the gaseous environment. Furthermore, the fast response time in detection is complemented by a fast recovery time back to nearly the baseline level prior to any VOC exposure.

In one embodiment of the present invention, chemical reactants are included in the nanofibers that can react with the sorbed VOCs or gases in the fiber. In these instances, the product of the reactant interacts with the polymer itself (or other inclusions present in the nanofiber) to dramatically increase its conductivity. For instance, organic and inorganic iodine compounds that will react with ozone and generate iodine (such as potassium iodide) can be used in one embodiment as the reactant in a PMMA/fullerene or a PMMA/SWCN nanofiber system intended for ozone detection. Iodine is liberated in the reaction with ozone and combines with the fullerene or the SWCN to form an intercalated complex that has a dramatically increased electrical conductivity. Another embodiment of the present invention utilizes conducting polymers or conventional polymers that have unsaturated C=C double bonds that will be oxidized by ozone, leading to the cleavage of the double bond and change the electron delocalization and induce a decreased conductivity of the material.

Other reagents that react rapidly with ozone can also be used and serve to modify the conductivity of the polymer to different extents. The reactants can be included in a conducting polymer nanofiber or in a conventional polymer nanofiber that is rendered electrically conductive by the addition of some form of carbon. The approach utilizes a chemical change in the fiber matrix as opposed to a reversible physical change; therefore the fiber matrix will slowly deteriorate with reaction and will eventually need to be replaced. In some instances with other reagent/reactant systems, a reversible reaction that regenerates the reactant is possible.

In one embodiment of the present invention, the above-noted fibers or constituents included in them, designed to undergo a chemical reaction to modify their electrical conductivity, are part of a disposable fiber sensor element which could be replaced on an electronics unit detecting for example ozone. Accordingly, in this embodiment, a user would after exposure and/or warning of exposure, install a new fiber sensor element before re-entering an environment subject to ozone exposure. Alternatively, the lifetime of the chemical reaction and the concomitant conductivity change would be predetermined ahead of time, and the electronics unit would inform the user of the exposure sensitivity remaining on the sensor.

In another embodiment of the present invention, the fiber sensor and electronics unit are disposable.

Figure 8:
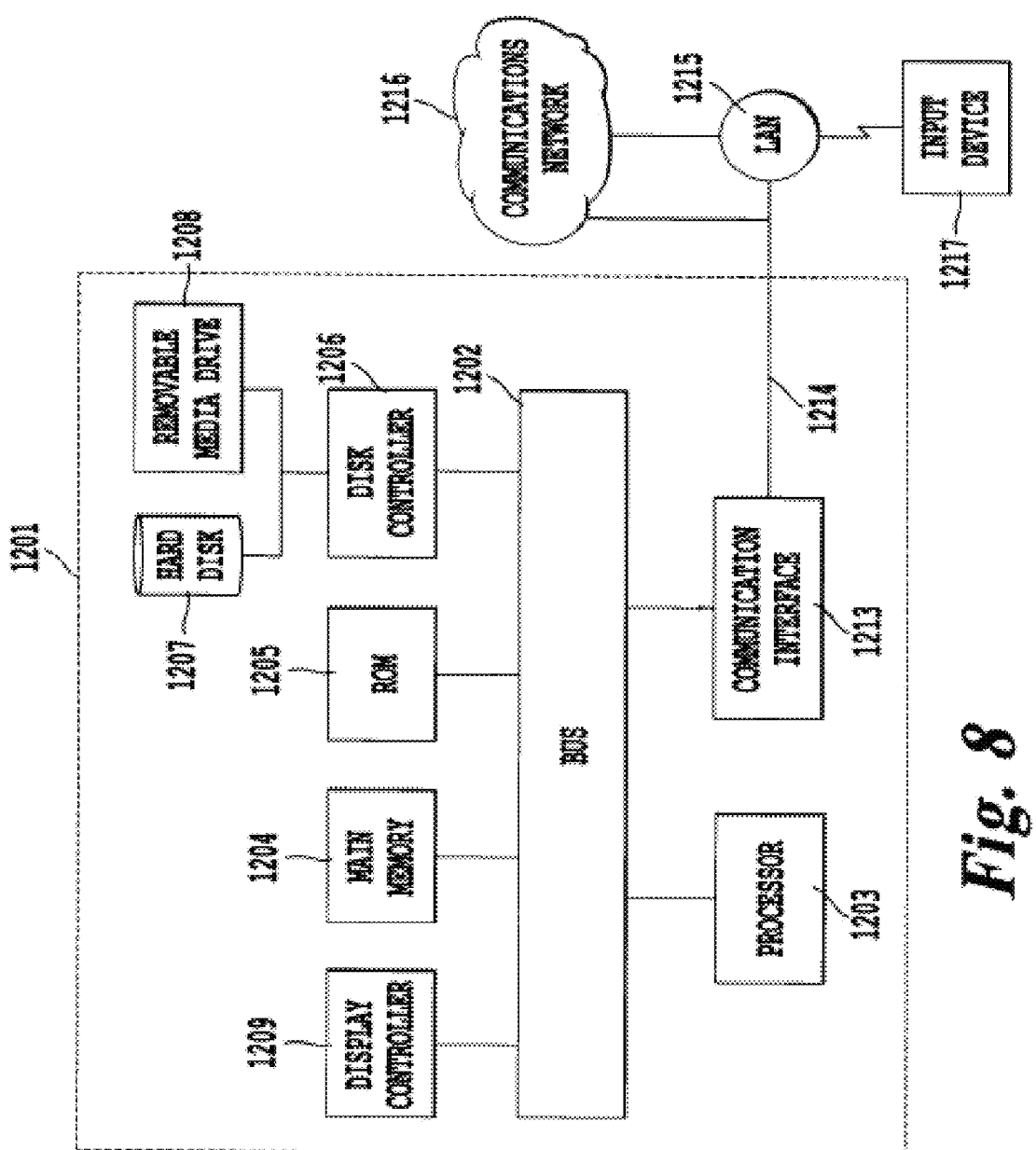
FIG. 8 is a schematic illustration showing computer system according to one embodiment of the present invention.

FIG. 8 illustrates one embodiment of a computer system 1201 in which the analyzer 18 of the present invention can be implemented. The computer system 1201 is programmed and/or configured to perform any or all of the functions described above. In particular, the computer system depicted in FIG. 8 is capable of executing a number of programs designed to implement a "finger print" recognition of the sensor signature based on learned responses in which known volatile species are catalogued. The computer system depicted in FIG. 8 can then, based on these learned responses, embodied for example in analyzer 18 of the present invention can determine if the observed response matches a particular species of interest, and based on the magnitude of the response determine a concentration level of the species.

U.S. Pat. Nos. 6,680,206 and 6,289,328 (the entire contents of which are incorporated herein by reference) provide details on the development of a system to learn respective responses, as would be applicable in the present invention for particular VOC and fiber-types chosen.

Improved Membrane Performance

In one embodiment of the invention, the sensors described herein and below are used to sense a chemical signature of a droplet on a surface of a membrane protected electrospun polymer nanofiber mat. In this embodiment, the membrane serves the following two functions:
1. protects sensor by preventing damage from physical contact and provides chemical resistance to the nanofiber sensing material, and
2. enhances sensor selectivity by virtue of its partitioning coefficients to selectively exclude certain chemicals before reaching to sensing material.

The composition of the membrane material can be any polymer, including hydrophobic silicone material, such as polydimethylsiloxane (PDMS) discussed above. Also, the protective membrane can be in forms of either a nonporous film or a porous thin film or a layer of electrospun polymer nanofibers which is formed on a mat of nanofibers.

The inventors have discovered that a silicone membrane of a sufficient thickness to improve the ruggedness of the sensing material can be used without serious degradation in the sensing performance. Moreover, it has been found that the silicone membrane selectively allows molecules evaporating from the droplet to penetrate through membrane material, which in turn further enhances the selectivity of the sensor system.

In one example, poly(methyl methacrylate) (PMMA)/5 wt % single wall carbon nanotubes (SWCNTs) was used as the nanofiber sensing material, which was coated with silicone membranes with different thicknesses. "Neat methyl salicylate" (a mustard agent simulant) and water droplets were used as analytes, which were deposited directly on the silicone membrane protecting the sensing material. It was observed that, with the silicone membrane, the sensing material showed response to both methyl salicylate and water droplets (FIG. 11) from increase of the electrical resistance of the sensing material soon after the analyte droplets were placed on the surface.

Figure 10A:
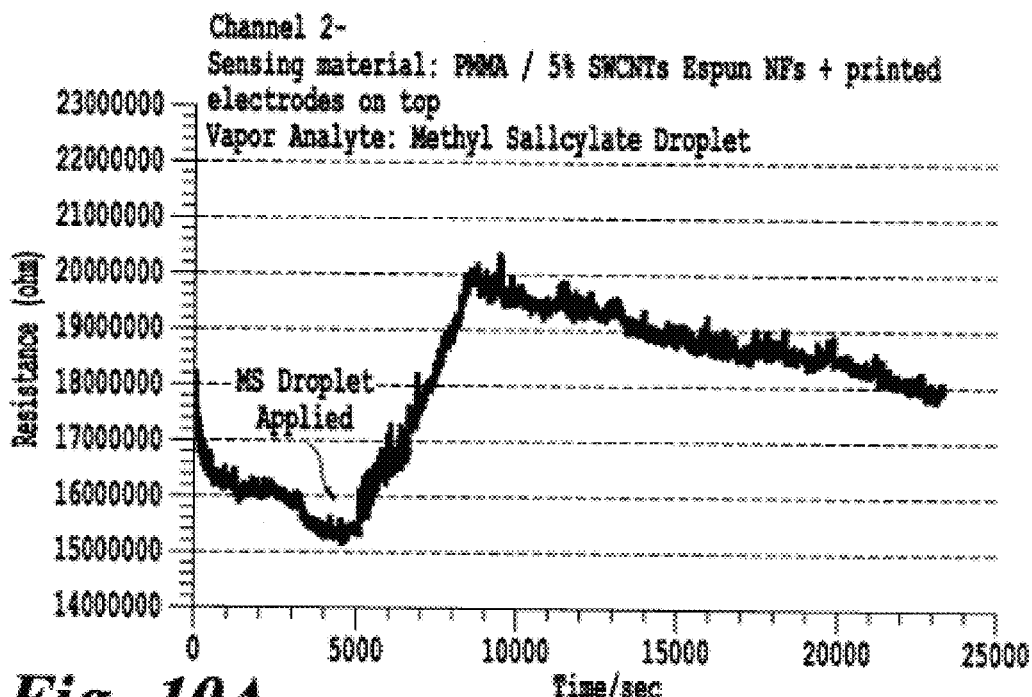
FIGS. 10A and 10B are depictions of respective response profiles of a nanofiber sensing material exposed to methyl salicylate (FIG. 10A) and water (FIG. 10B) droplets.
Figure 10B:
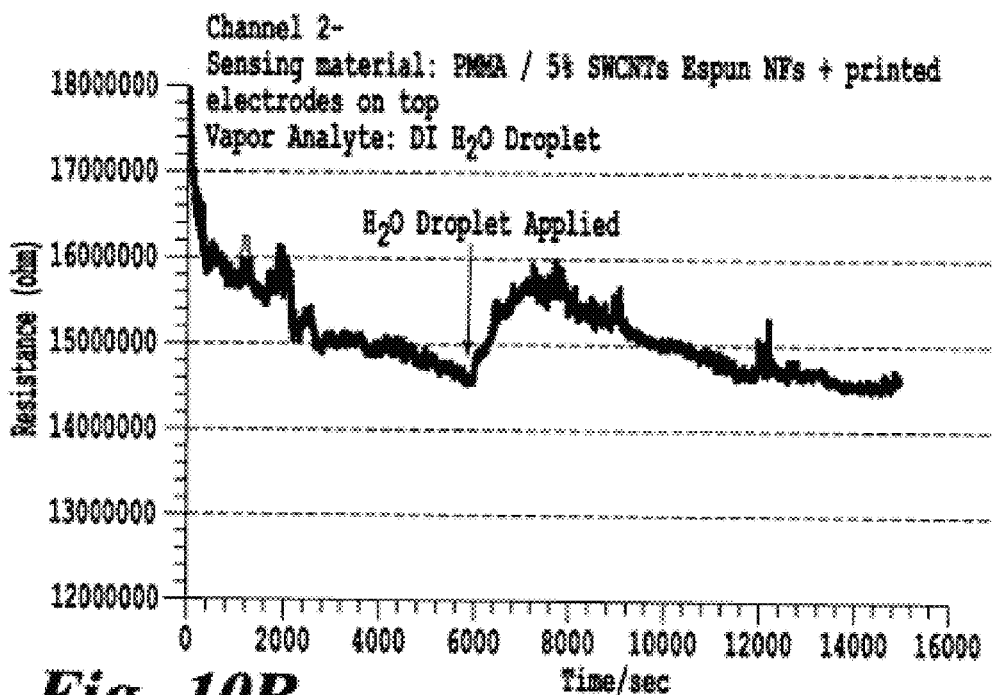

FIGS. 10A and 10B are depictions of respective response profiles of a nanofiber sensing material exposed to methyl salicylate (FIG. 10A) and water (FIG. 10B) droplets. A protective silicone membrane (0.017" thick) was used in both tests. The sensing material showed more than 4 times higher response to the methyl salicylate droplet than to a water droplet. This indicates that the polymer sensing material is much more sensitive to methyl salicylate. In one embodiment of this invention, polymers and protective membranes may be selected to have a lower sensitivity for water. For example, by selecting a hydrophobic membrane, the effects of water as a chemical species exposed to the sensor can be reduced or eliminated. Additionally, as noted above, each sensor may respond in a different way for different chemical species exposure. Pattern recognition can be used to evaluate the responses and through predetermined, programmed, or learned patterns and can be used to ascertain the chemical species exposed to the sensor.

Figure 11:
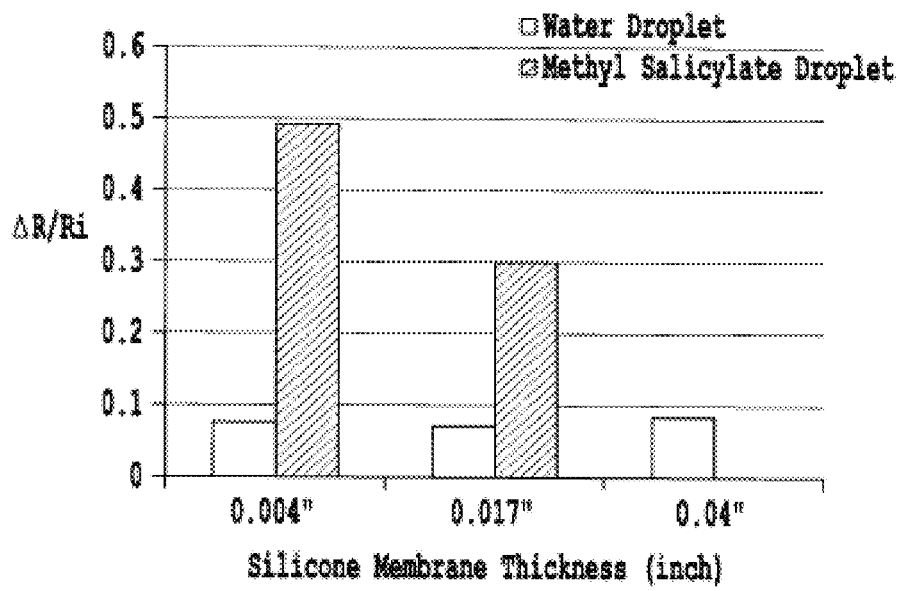
FIG. 11 is a graphical depiction of results for silicone membranes with three different thicknesses.

FIG. 11 is a comparison of sensor responses to water and methyl salicylate droplets covered with silicone membranes of different thicknesses. The y axis indicates relative resistance change of the sensor with an analyte droplet on membrane surface. More specifically, in FIG. 11, results are shown for silicone membranes with three different thicknesses of 0.004", 0.017" and 0.04". It was observed that the sensor response to water droplet was similar for the three different membrane thicknesses. This seems reasonable because the membrane material is hydrophobic, the water vapor will have minimum penetration through the membrane. However, the response to methyl salicylate droplets decreased with increased membrane thickness.

These results imply that the partitioning coefficient for methyl salicylate vapor in the membrane is such that the effect depends on the thickness of the membrane. The implication of this discovery is that, in addition to serving to protecting the nanofiber sensing material, the selectivity of the membrane material could also be selected to complement the sensor selectivity. Therefore, the selectivity of the membrane-sensing material system will provide additional options to allow tuning for analytes of interest.

It is worth noting that even though the silicone membranes stay intact after 5 to 10 repetitive droplet tests, the nanofiber sensing material partially deteriorates from the penetration of methyl salicylate (in some cases condensation of methyl salicylate on the sensor). Accordingly, in one embodiment of this invention, the sensing membrane along with protect membrane is designed as a disposable insert or as part of a disposable device.

Electrospun polymer nanofiber mats can also be used as protective membrane layer for protection of the nanofiber sensing material. As shown in FIG. 12B below, pure PMMA nanofiber was electrospun onto nanofiber sensing material before electrode deposition. In this embodiment, the nanofiber layer provided an excellent protective layer to prevent deteriorating of the nanofiber sensing material when in contact with conductive printer ink. In addition, compared with hydrophobic silicone membrane material, an electrospun nanofiber layer is more gas permeable because of the porous nanofiber packing structure, thus should improve response time of the sensor.

Figure 12A:
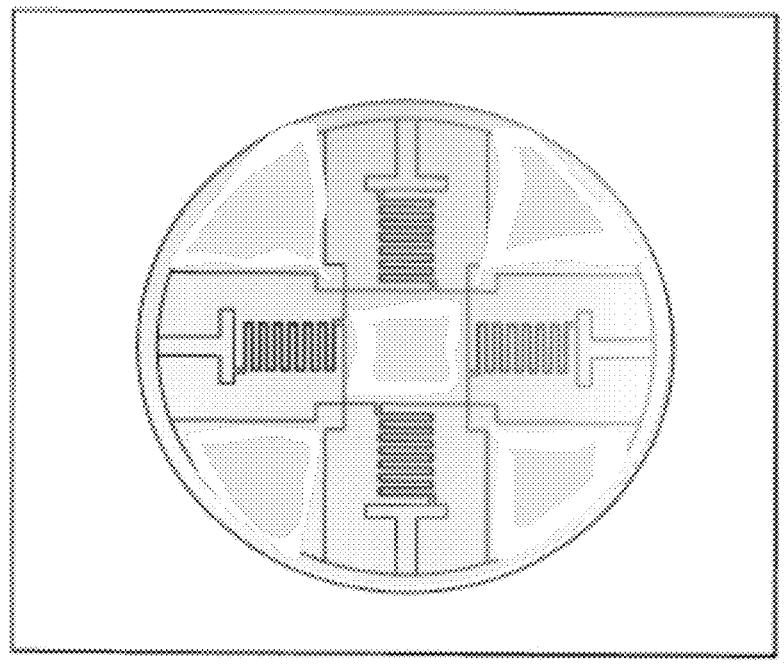
FIGS. 12A and 12B are depictions of poly(benzyl methacrylate) (PBeMA) nanofiber materials with printed electrode: without a PMMA protective coating layer FIG. 12A; with PMMA surface protective coating layer FIG. 12B.
Figure 12B:
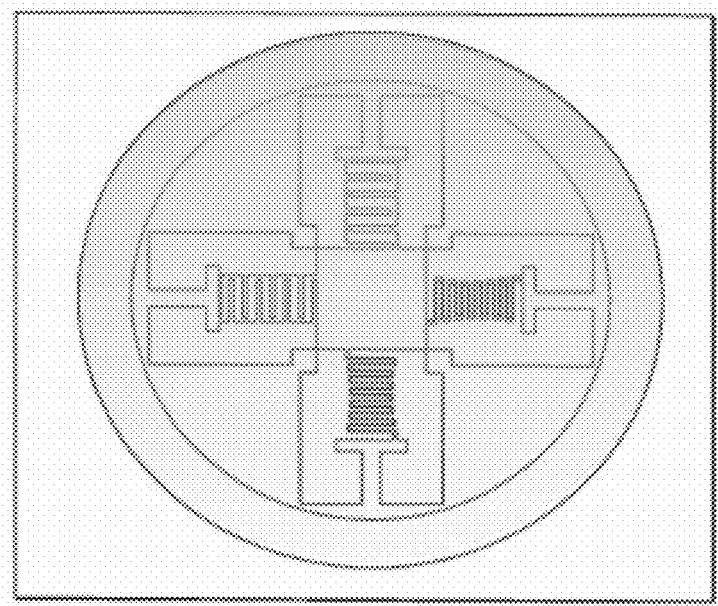

FIGS. 12A and 12B are depictions of poly(benzyl methacrylate) (PBeMA) nanofiber materials with a printed electrode: without a PMMA protective coating layer in FIG. 12A; with PMMA surface protective coating layer overlaying the PBeMA nanofiber sensing material in FIG. 12B. The layer-by-layer construction of the PMMA protected sensing material is: $1^{st}$ layer (bottom layer): Teflon membrane; $2^{nd}$ layer (middle layer): PBeMA nanofiber layer; $3^{rd}$ Layer (top layer): PMMA top coating layer. One design criteria for the nanofiber sensor is the compatibility between the inks and the material of the nanofiber sensor. For example, PBeMA polymer nanofiber is not compatible with some material printer conductive inks (e.g. Silver conductive ink). In this case, a protective layer (e.g. PMMA nanofiber layer in FIG. 12B) can reduce or eliminate ink interactions with the nanofibers. Alternatively, in one embodiment, conductive inks can be used in this invention which would not present a compatibility issue with polymers selected. For example, Orgacon™ Transparent conductive ink, IJ-1005 (made of Poly(3,4-ethylenedioxythiophene)-poly(styrenesulfonate) in water with a low percentage of Diethylene Glycol) has been found to be compatible with PMMA and Polyurethane polymer nanofibers with minimum alteration of the nanofiber morphology.

Signal Processing with the Electronic Nose

The computer system depicted in FIG. 8 may be in communication with other processors and computers via the communications network 1216 (discussed below). The computer system 1201 includes a bus 1202 or other communication mechanism for communicating information, and a internal processor 1203 coupled with the bus 1202 for processing the information. The computer system 1201 includes a memory 1204, such as a random access memory (RAM) or other dynamic storage device (e.g., dynamic RAM (DRAM), static RAM (SRAM), and synchronous DRAM (SDRAM)). The computer system 1201 preferably includes a non-volatile memory such as for example a read only memory (ROM) 1205 or other static storage device (e.g., programmable ROM (PROM), erasable PROM (EPROM), and electrically erasable PROM (EEPROM)).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)) that are especially designed to process analog signals and convert the analog signals to the digital domain.

The computer system 1201 also includes a communication interface 1213 coupled to the bus 1202. The communication interface 1213 provides a two-way data communication coupling to a network link 1214 that is connected at least temporarily to, for example, a local area network (LAN) 1215, or to another communications network 1216 such as the Internet during downloading of software to the processor 24. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented as part of the communication interface 1213 to provide data exchange. In any such implementation, the communication interface 1213 sends and receives electrical, electromagnetic or optical signals that carry digital data streams representing various types of information. Such communications are applicable in various of the embodiments of the present invention, where the analyzer 18 is linked to network resources for example permitting data files and program resources to be shared. Moreover, the analyzer 18 may be in communication with other analyzers forming a network of sensors monitoring for chemical species. Moreover, the analyzer 18 may be in communication with global positioning satellite (GPS) information for cases where the sensor of the present invention is on a mobile platform.

Figure 9:
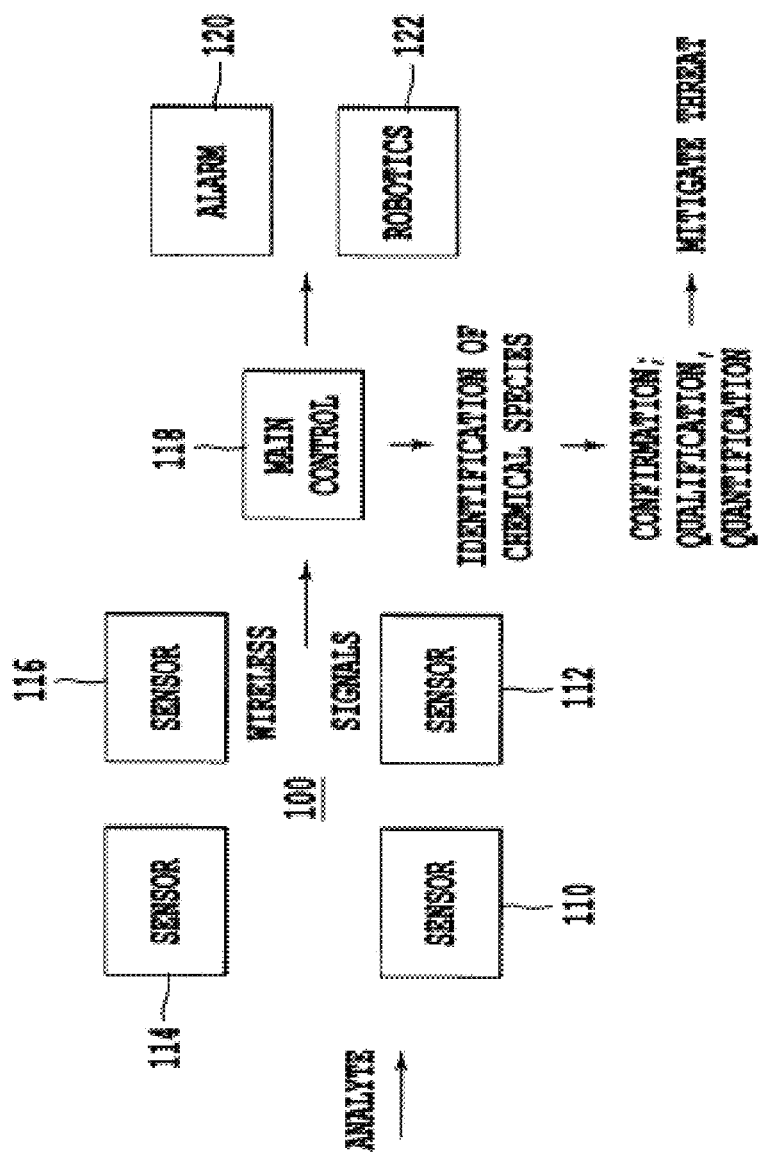
FIG. 9 is a schematic illustration showing an example of a network of chemical sensors according to one embodiment of the present invention.

Indeed, in one embodiment of the present invention there is provided a network of sensors, as shown for example in FIG. 9. One example could be a network of building alarm system. Each individual room is equipped with a chemical sensor of the present invention. When there is toxic gas at alarm level has been detected, the chemical sensor will send out alarm signal to the main control unit, then trigger the building alarm system. FIG. 9 is a schematic illustration showing a network 100 of chemical sensors according to one embodiment of the present invention. In this illustration, multiple sensors (ie., a network) are placed at distinct sites 110, 112, 114, and 116 (for example in different rooms in a building). The sensors are connected by a network (such as the LAN 1215 shown in FIG. 8) to a main control 118. The main control 118 can be configured to activate alarm 120 should the concentration of VOCs exceed a predetermined threshold.

In one embodiment of the present invention, the network can continuously monitor for example a sensor array conductivity profile and respond to specific pre-identified trigger patterns by implementing second level sensors to confirm the presence of volatile or remotely implement mitigation tasks. Mitigation tasks can range from identification of concentration profiles for the suspect VOC to control of robotic equipment to mitigate threat.

In one embodiment of the present invention, chemical sensors utilizing the features described above can be integrated with robotics 122 to produce chemotactic devices that are cable of following a plume or seek the origin of specific odorants in a geographic region. Such sensors and others described above in the various embodiments of the present invention can be provided with integrated electronic components permitting continuous monitoring of a sensor conductivity profile in order to respond to specific pre-identified trigger patterns, allowing for rapid detection of chemical species. The integrated electronics can include a wireless communication module (such as for example the communication interface 1213 and the network link 1214 in FIG. 8) to form a distributed network of sensors.

Applications of the Electronic Nose Sensor

In other application areas, the ability of the present invention to print electrodes in fabrics and to electrospin appropriate fibers with the printed electrodes permits in one embodiment of the present invention the construction of wearable sensors.

Such wearable sensors have a variety of applications from sensors in health care patients where the sensors are on wound dressings, thereby permitting the recording over time the progress of patient in recovery from open wounds where infections may develop. The sensors would be connected to a remote diagnostic system for acquisition, processing, and control of the sensor. Another application in the health care field of the sensor patch would be in the monitoring of sweat or other body fluids, or expelled breath for metabolic byproducts indicating physiological stress or disease. Another application would be to use the sensors to monitor soldier stress by monitoring of sweat or other body fluids, or expelled breath for metabolic by-products indicating physiological stress.

As described in the '282 application incorporated by reference as noted above, the nanofiber mat materials can be electrospun using polymers including catalytic metal particles (e.g., nanoparticulate metal and metal oxide nanoparticles) that would provide the mechanism for catalysis. Further, as described in U.S. Ser. No. 11/130,269, these nanoparticles can be incorporated into the fibers of the fiber mat during electrospinning. Alternatively, these particles could be added to fibers (containing no particles as electrospun) during formation of the fiber mat, or added after formation of the fiber mat.

Owing to the small diameter of the nanofibers and the low resistance to fluid flow, the nanofiber mats offer advantages over traditional catalyst media and prior art nanofiber-based catalyst materials in that the available surface area for catalytic reactions can be increased over the prior techniques. The inclusion of nanoparticulate metal and metal oxide nanoparticles in the nanofiber can yield a valuable catalytic material for industrial and biological processes.

Similarly, in wound dressings, the nanofiber mat materials of the present invention would be electrospun using biocompatible or biodegradable polymers to provide nanofiber mats which permit free exchange of gases. Further, similar to that described for example by Katti, D. S., K. W. Robinson, et al., "Bioresorbable nanofiber-based systems for wound healing and drug delivery: Optimization of fabrication parameters," nanofiber mats can retard the ingress of microbes into the wound surface. The fiber mats can therefore be used as effective wound dressings, especially when added functionality such as haemostasis and controlled drug delivery is built into the structure. Further, as described in U.S. Ser. No. 11/130,269, nanoparticles can be incorporated into the fibers of the fiber mat during the fiber mat formatting or after fiber mat formation as described above. Such nanoparticles can be drug particles designed to release a drug as the fiber mat dissolves over time.

Similarly, in scaffolding for tissue engineering, the nanofiber mat materials would be electrospun using biodegradable polymers to provide nanofiber mats which would be used to culture cells within the structure. Once the cells have proliferated, the fiber mat scaffold would be surgically implanted in the body. The high surface area of nanofibers promotes cell attachment, and the high porosity of the construct allows exchange of gases and nutrients.

Similarly, in drug or bioactive material delivery applications, the nanofiber mat materials would be electrospun using water soluble polymers to provide nanofiber mats which including the above-noted particles (now containing more generally bioactive substances) would be used to provide a controlled delivery of the bioactive substances. Pharmaceuticals, especially those that are sparingly soluble in water can be delivered using nanofiber devices. The drug compound either dissolves or is distributed as fine particles in the polymer nanofiber matrix. Under physiological conditions, the bioactive agent is released either diffusively or via biodegradation of nanofiber matrix.

Similarly, in antibacterial nanofiber mats application, the nanofiber mat materials would be electrospun using polymers that would additionally include photocatalytic compounds such as titania, similar to that described for example by Kenawy, E. R. and Y. R. Abdel-Fattah, "Antimicrobial properties of modified and electrospun poly(vinyl phenol)." Particles of the photocatalytic compounds could be included as discussed above by addition of particles of these photocatalytic compounds during formation of the fiber mat or after formation of the fiber mat. Exposure of the fiber mat to light in this application produces free-radical species that are biocidal. The same can also be achieved by dispersion of nanoparticles such as those of silver in the nanofibers. In this application, the electrospun fibers would be substantially transparent to the light permitting production of free radicals even in the interior to the fiber mat.

Similarly, in textile applications, electrospun nanofibers would be deposited on conventional textile fabrics or incorporated as a component in a multi-layered fabric construct. Inclusion of a nanofiber mat in a textile as a member will enhance the particle filtration effectiveness of the textile material. The nanofiber layer would not only serve as the most-effective filter layer in such a construct, but would also not impact 'breathability' of the material as nanofiber mats allow transport of air and moisture through the textile. This application area has interest not only from an environmental standpoint of protecting individuals from dermal exposure to particulates including nanoparticles, but also in military applications where dermal exposure to particles carrying biologically active materials or chemical agents need to be controlled.

In these applications, the fiber mats are attached to a support or detachable therefrom. The support can be the support used for production of the fiber mat or can be a detachable support permitting for example in the wound dressing application the removal of the support from the injury sites.

Other applications include for example wearable sensors on the attire of miners working in closed spaces and susceptible to exposure to explosive or toxic gases.

In other applications, the sensors can be integrated into solider garments to detect chemical and biological warfare agents. Particularly, the encased membrane e-nose system will be programmed to detect droplets of chemical agents. The encased membrane e-nose system can provide a signal under dark conditions and not require interpretation. The encased membrane e-nose system can provide detection of semivolatile droplets over the front surface of the sensor. Civilian applications would include the measurement of pesticide droplets for hygiene purposes and measurement of fuel droplets for safety purposes.

Referring to FIG. 11, the maximum membrane thickness used prior to this invention as vapor concentrator was limited to 2 µm. Here, the membrane thickness is in the range of 50 µm to 5 mm. In this range of thickness, one would have normally expected the sensitivity of the fibers underlying the membrane to decrease and become unusable. However, the present inventors have found this expected effect not to be true. Transmission through the membrane appears to depend on the partitioning coefficients of the material. Moreover, the thicker membranes used here not only unexpectedly show acceptable changes in electrical resistance when exposed to the semivolatile droplets but also provide a useable support for the nanofibers shielding the nanofibers from physical shock and direct mechanical damage as would occur in many applications.

In one embodiment of the invention, the composite polymer nanofiber sensing material can be partially covered by protecting/selecting membrane layers with different thicknesses. Depending on the interaction of the sensing material with interested vapor analyte, protective membrane with different thickness can be applied on the sensing material surface. For example, one half of the sensing material could be covered by a thin protective layer for vapor detection (e.g., less than 2 µm), while the other half is covered by thick protective membrane layer for droplet detection (e.g., between 5 µm and 5 mm). In addition to using membranes with different thickness on regions of the surface, membranes with different chemical and physical characteristics such as partitioning coefficients can be utilized to increase the specificity of the sensor.

Stacked Sensor Configurations

In one embodiment of this invention, a multiple sensor configuration is utilized. In one aspect of this embodiment, a stacked sensor configuration is used. In another aspect of this embodiment, a laterally-spaced sensor configuration can be used. A range of different polymers with unique sensitivities to desired families of compounds could be used in a single open-end cylinder sensor to target class of compounds (e.g. chemowarfare agents, TICs, etc.), as shown in FIGS. 13A and 13B.

Figure 13A:
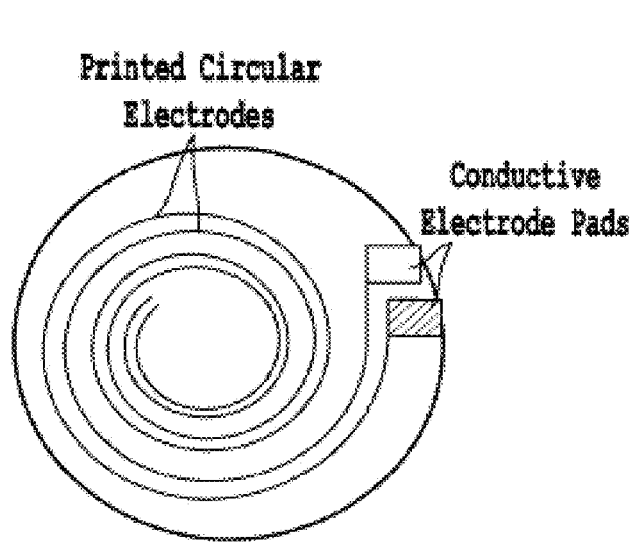
FIG. 13A is a schematic illustration of printed conductive electrode with circular electrode pattern.

More specifically, FIG. 13A is a schematic illustration of printed conductive electrode with circular electrode pattern. While not shown in FIG. 13A, the fibers are contained preferably under (but could be disposed on top of) the printed conductive electrode patterns. FIG. 13B is a passive air flow sensor device utilizing as stacks of separate devices the printed conductive electrode shown in FIG. 13A. Sensor patches (i.e., partitioning/protective membrane, conductive electrode pattern and sensing fibers and supporting membrane) are stacked on top of each other forming separate devices. On one or more of these separate devices, the conductive electrode patterns are arranged to form a spiral within the circular configuration with the distance between the two conductors kept constant. The connections to the electrodes are at the outer perimeter of the circular configuration.

The electrode connection is designed on the open end-side cylinder chamber for conductivity measurements. The side electrode connections allow stacking the sensor patches with angular off-sets to allow electrical connections without physical interference. The sensing materials/patches in one embodiment are disposed in a stacked configuration inside a tube in FIG. 13B. The advantage of a sensor stack and/or tubular design is that the sensor can function as a passive flow through sensor if used in a moving airstream such as in an air duct or attached to a moving vehicle without the necessity of a pump requirement, although pumping could be used. The electrode in one embodiment is designed as circular. However other designs such square, rectangular, or other geometrical patterns are suitable and can maximize the sensor layout geometry.

Figure 13B:
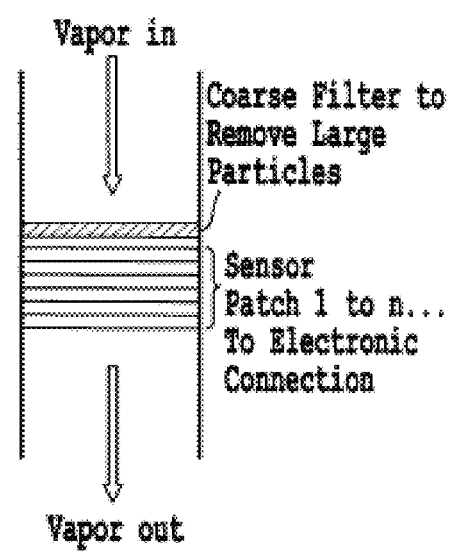
FIG. 13B is a passive air flow sensor device utilizing as stacks the printed conductive electrode patterns shown in FIG. 13A.

FIG. 13B also illustrates the principle of a pre-filter where a coarse filter or membrane is used to prevent deposition of large particles in the sensor. The pre-filter is selected to remove interfering particles but not to remove analytes of interest.

FIG. 13B also illustrates the utility of stacking the sensor patches to improve the specificity of the detector taking advantage of the flow-through properties of the sensing materials. The selection of a specific polymer for the sensing material allows response with specific classes of organic material in a stacked configuration in a way similar to that of a parallel configuration illustrated in FIG. 3A and allows for example neural network interpretation of the signal to improve specificity.

In one embodiment of this invention, the stacking of sensor patches as shown in FIG. 13B is used advantageously in a predetermined order. The sensor patches in this configuration can detect a family of organic compounds by selectively absorbing these materials on different ones of the sensor patches. Therefore, the sensor patches first in the stack may remove materials that might affect the last sensor patches in the stack, thereby improving the selectivity of the sensor stack configuration.

Laterally-Spaced Sensor Configurations

Figure 14:
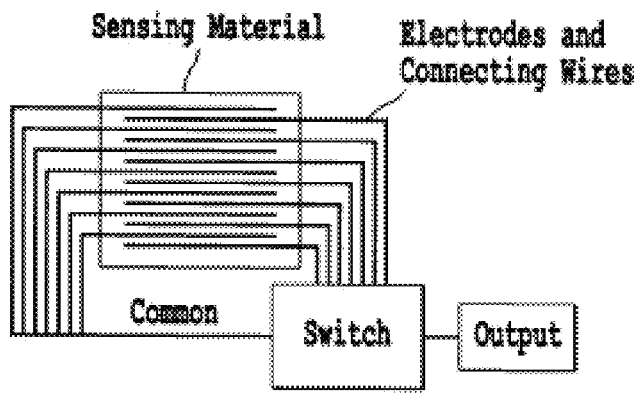
FIG. 14 is a depiction of one example of a laterally-spaced sensor configuration for 2-dimensional spatial detection.

FIG. 14 is a depiction of one example of a laterally-spaced sensor configuration for 2-dimensional spatial detection. Utilization of this detection configuration would be ideal when the droplet to be detected is round in shape and when the droplet is symmetrical. However, the sensor can still be utilized with non-idealized droplets. In this configuration, the binary information is obtained from a switch. In this configuration, with the electrode spacing defined, lateral sensors showing a response indicative of the presence of the detected species. The number of adjacent lateral sensors showing a response provide an indication of the droplet size. If only one set of electrodes indicates the presence of a droplet, then the droplet is smaller than the separation distance between the electrodes. If two adjacent sets of electrodes simultaneously indicate a presence of a droplet then the droplet is smaller than the combined distance spanned by the two electrodes. The dimension of the droplets would be scaled by the number of electrodes spanned and the size resolution would be limited by the separation between electrodes. Uncorrelated signals would indicate discrete droplets.

Accordingly, one utility of this invention would be for the detection and sizing of droplets for chemical warfare or pesticide applications. In this configuration, two-dimensional information (-y, time information) can be obtained.

Figure 15:
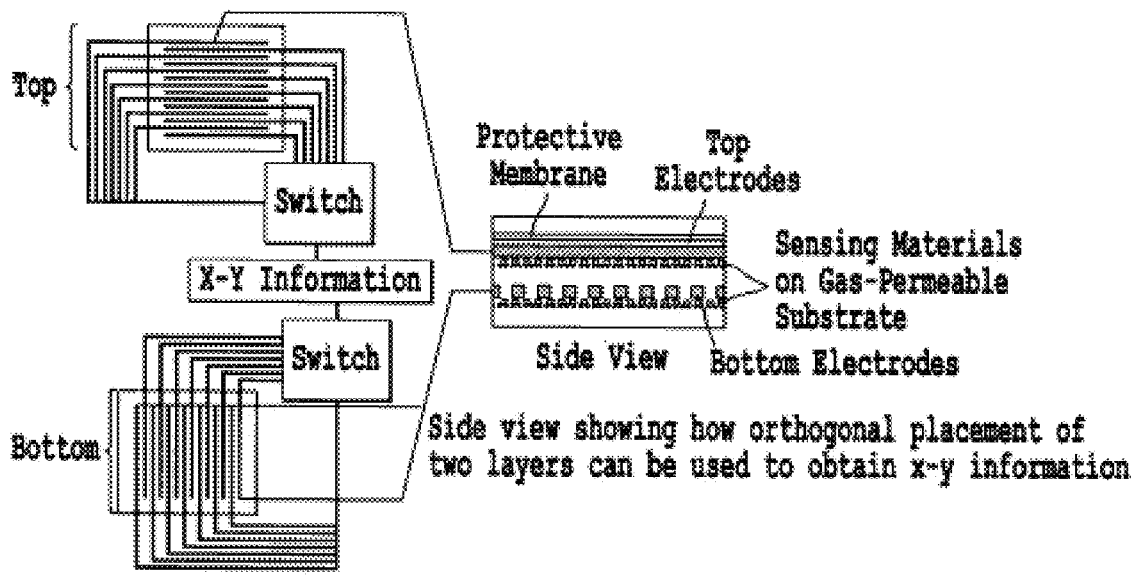
FIG. 15 is a depiction of one example of a laterally-spaced sensor configuration for 3-dimensional spatial detection.

FIG. 15 is a depiction of one example of a laterally-spaced sensor configuration for 3-dimensional spatial detection, x,y, time. 3-D dimension droplet spatial information of the droplet can be obtained from this design(X-Y dimension and time). This design is a stack design. Nanofiber sensing material is electrospun on to a gas permeable substrate (e.g. coarse polymer thin film, espun nanofiber mat, etc.) and then the electrodes are deposited on nanofiber sensing material. During sensing process, droplets hit the top layer (a first sensor patch) first, penetrate through the sensing material and the gas permeable substrate, then reach to the bottom layer electrodes (a second sensor patch). The device operates in the same manner of the 2-D system in FIG. 14. The correlation of adjacent electrodes for simultaneous responses indicates the impact of a droplet and can be used to determine the droplet size. The utility of the 3-D would be to detect stratification of droplets by gravity sedimentation in a flowing gas duct or by the pattern of droplets on a horizontal sensor device the direction of the source of the droplets could be assessed.

In various of the spatial sensor positions in the configurations described above, a hydrophobic or hydrophilic membrane layer can be used to selectively absorb or exclude certain class of compounds, thus permitting more detailed knowledge of the ambient droplets. Moreover, a pre-filter layer (as shown in FIG. 13) can be used to remove large particles and dust particles. The material can be also hydrophilic that selectively absorb water vapor, then to be disposed after use.

Numerous modifications and variations of the present invention are possible in light of the above teachings. It is therefore to be understood that within the scope of the appended claims, the invention may be practiced otherwise than as specifically described herein.

The invention claimed is:

1. A chemical wearable sensor comprising:
   at least one chemical sensor integrated with a fabric, the at least one chemical sensor configured for collection and identification of a chemical identity of at least one liquid droplet incident on the at least one chemical sensor, the at least one chemical sensor having,
   a plurality of sensing fibers disposed with the fabric,
   a set of electrodes connected to the plurality of sensing fibers at spatially separated points to permit an electrical impedance of a circuit connected to the plurality of sensing fibers to be measured, and
   a protective membrane encasing the plurality of sensing fibers, having a thickness which prevents damage from physical contact, holding the at least one liquid droplet apart from the plurality of sensing fibers, and allowing chemical species from the at least one liquid droplet to selectively penetrate through the protective membrane, wherein a lateral space exists between each of the electrodes, the protective membrane non-conformally bridges over lateral space between the electrodes, and the protective membrane separates the at least one liquid droplet from the set of electrodes.

2. The sensor of claim 1, further comprising:

a processor in communication with a circuit connected to the plurality of sensing fibers, and configured to:

measure a response in the electrical impedance from the set of electrodes in the presence of the at least one liquid droplet; and determine from the response the chemical identity of the at least one liquid droplet.

3. The sensor of claim 1, wherein the fabric comprises antibacterial fibers including photocatalytic compounds which, when activated by light, produce biocidal free-radical species.

4. The sensor of claim 1, wherein the fabric comprises photocatalytic compounds and the plurality of sensing fibers comprise fibers transparent to light.

5. The sensor of claim 1, wherein the fabric comprises a textile having the plurality of sensing fibers integrated into the textile.

6. The sensor of claim 5, wherein the textile comprises a multi-layered fabric.

7. The sensor of claim 1, wherein the fabric comprises catalytic compounds comprising at least one of titania and silver.

8. The sensor of claim 1, wherein the fabric comprises catalytic compounds comprising nanoparticulate metal and metal oxide nanoparticles.

9. The sensor of claim 1, wherein the plurality of sensing fibers comprise electrically conductive fibers.

10. The sensor of claim 9, wherein the electrically conductive fibers comprise gas-absorbing fibers.

11. The sensor of claim 1, wherein the plurality of sensing fibers comprise nanofibers having an average fiber diameter less than 1000 nm or less than 100 nm.

12. The sensor of claim 1, wherein the plurality of sensing fibers have an electrical impedance which changes due to at least one of an increase in volumetric size of the sensing fibers by sorption of the chemical species or a change in electrical conduction by a chemical reaction of the chemical species with a material of the sensing fibers.

13. The sensor of claim 1, wherein the protective membrane comprises a disposable membrane.

14. The sensor of claim 1, wherein the protective membrane comprises fibers embedded therein which are separate from the plurality of sensing fibers.

15. A chemical wearable sensor comprising:

at least one chemical sensor integrated with a fabric, the at least one chemical sensor configured for collection and identification of a chemical identity of at least one liquid droplet incident on the at least one chemical sensor, the at least one chemical sensor having, a plurality of sensing fibers disposed with the fabric, a set of electrodes connected to the plurality of sensing fibers at spatially separated points to permit an electrical impedance of a circuit connected to the plurality of sensing fibers to be measured, and a protective membrane encasing the plurality of sensing fibers, having a thickness which prevents damage from physical contact, holding the at least one liquid droplet apart from the plurality of sensing fibers, and allowing chemical species from the at least one liquid droplet to selectively penetrate through the protective membrane, wherein the thickness of the protective membrane ranges from 50 µm to 5 mm.

16. The sensor of claim 15, wherein the at least one chemical sensor comprises an array of chemical sensors comprising a first gas permeable sensor and a second gas permeable sensor.

17. The sensor of claim 16, wherein the first gas permeable sensor and the second gas permeable sensor comprise a stack of sensors serially stacked on top of each other with the protective membrane above the stack, the first gas permeable sensor comprises a plurality of first sensing fibers and a first set of first electrodes connected to the plurality of first sensing fibers, and the second gas permeable sensor comprises a plurality of second sensing fibers and a second set of second electrodes connected to the plurality of second sensing fibers.

18. The sensor of claim 17, wherein the first set of first electrodes of the first gas permeable sensor are disposed on top of the second set of second electrodes, and the first electrodes of the first set of first electrodes have an orientation rotated around a top-to-bottom direction of the stack from the second electrodes of the second set of second electrodes of the second gas permeable sensor.

19. The sensor of claim 15, wherein the protective membrane directly contacts both the electrodes and the plurality of sensing fibers, and the set of electrodes are disposed directly on the sensing fibers with the protective membrane disposed directly on the electrode.

20. A chemical sensor comprising:

at least one chemical sensor integrated with a substrate, the at least one chemical sensor configured for collection and identification of a chemical identity of at least one liquid droplet incident on the at least one chemical sensor, the at least one chemical sensor having, a plurality of sensing fibers disposed with the substrate, a set of electrodes connected to the plurality of sensing fibers at spatially separated points to permit an electrical impedance of a circuit connected to the plurality of sensing fibers to be measured, and a protective membrane encasing the plurality of sensing fibers, having a thickness which prevents damage from physical contact, holding the at least one liquid droplet apart from the plurality of sensing fibers, and allowing chemical species from the at least one liquid droplet to selectively penetrate through the protective membrane, wherein a lateral space exists between each of the electrodes, the protective membrane non-conformally bridges over lateral space between the electrodes, and the protective membrane separates the at least one liquid droplet from the set of electrodes.

* * * * *